United States Patent
Serhan et al.

(10) Patent No.: US 11,020,406 B2
(45) Date of Patent: *Jun. 1, 2021

(54) COMPOSITIONS COMPRISING OMEGA-3 FATTY ACIDS, 17-HDHA AND 18-HEPE AND METHODS OF USING SAME

(71) Applicant: Solutex NA LLC, Miami, FL (US)

(72) Inventors: Charles Nicholas Serhan, Needham, MA (US); Fernando Moreno Egea, Alcobendas (ES); Joan Clària Enrich, Sant Esteve Sesrovires (ES)

(73) Assignee: Solutex NA LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/070,401

(22) Filed: Oct. 14, 2020

(65) Prior Publication Data

US 2021/0038614 A1 Feb. 11, 2021

Related U.S. Application Data

(63) Continuation of application No. 16/843,416, filed on Apr. 8, 2020, which is a continuation of application No. 15/757,023, filed as application No. PCT/US2016/050397 on Sep. 6, 2016, now Pat. No. 10,653,703.

(60) Provisional application No. 62/213,958, filed on Sep. 3, 2015.

(51) Int. Cl.
| | |
|---|---|
| A61K 31/557 | (2006.01) |
| A61K 31/202 | (2006.01) |
| A23L 33/12 | (2016.01) |
| A61P 29/00 | (2006.01) |
| C11B 3/00 | (2006.01) |
| C11B 1/10 | (2006.01) |
| A23D 9/00 | (2006.01) |
| C11C 3/10 | (2006.01) |
| A61K 45/06 | (2006.01) |

(52) U.S. Cl.
CPC ............ *A61K 31/557* (2013.01); *A23D 9/00* (2013.01); *A23L 33/12* (2016.08); *A61K 31/202* (2013.01); *A61K 45/06* (2013.01); *A61P 29/00* (2018.01); *C11B 1/104* (2013.01); *C11B 3/001* (2013.01); *C11C 3/10* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. |
| 4,501,728 A | 2/1985 | Geho et al. |
| 4,837,028 A | 6/1989 | Allen |
| 4,966,876 A | 10/1990 | Sankaran |
| 5,133,902 A | 7/1992 | Sankaran |
| 5,776,978 A | 7/1998 | Bruzzese |
| 6,284,268 B1 | 9/2001 | Mishra et al. |
| 7,259,006 B2 | 8/2007 | Komazawa et al. |
| 7,884,131 B2 | 2/2011 | Arterburn et al. |
| 8,735,111 B2 | 5/2014 | Vanhercke et al. |
| 9,238,634 B2 | 1/2016 | Arita et al. |
| 10,653,703 B2 | 5/2020 | Serhan et al. |
| 2009/0023808 A1 | 1/2009 | Raman et al. |
| 2009/0099260 A1 | 4/2009 | Senanayake et al. |
| 2009/0318394 A1 | 12/2009 | Nauroth et al. |
| 2011/0190389 A1 | 8/2011 | Arterburn et al. |
| 2012/0059061 A1 | 3/2012 | Arita et al. |
| 2013/0261180 A1 | 10/2013 | Gillies et al. |
| 2015/0126602 A1 | 5/2015 | Bannenberg et al. |
| 2015/0196521 A1 | 7/2015 | Manku et al. |

FOREIGN PATENT DOCUMENTS

| | | |
|---|---|---|
| CN | 1202068 | 1/2004 |
| CN | 1469858 | 1/2004 |
| CN | 100348184 | 12/2005 |
| JP | H01169354 | 7/1989 |
| JP | 6282586 | 7/2014 |
| KR | 2013/0135839 | 12/2013 |
| WO | WO 2002/102364 | 12/2002 |
| WO | WO 2005/089744 | 9/2005 |
| WO | WO 2006/055965 | 5/2006 |
| WO | WO 2013/170006 | 1/2014 |
| WO | WO 2014/209132 | 12/2014 |

OTHER PUBLICATIONS

Ariel et al., "Apoptotic neutrophils and T cells sequester chemokines during immune response resolution through modulation of CCR5 expression," Nat Immunol. 7(11):1209-16 (publication date: Nov. 2006, epublication date: Oct. 1, 2006).

Arita et al., "Resolvin E1, an endogenous lipid mediator derived from Omega-3 eicosapentaenoic acid, protects against 2,4,6-trinitrobenzene sulfonic acid-induced colitis," Proc Natl Acad Sci USA. 102(21):7671-76 (publication date: May 24, 2005, epublication date: May 12, 2005).

Arita et al., "Stereochemical assignment, anti-inflammatory properties, and receptor for the omega-3 lipid mediator resolvin E1," J Exp Med. 201(5):713-22 (publication date: Mar. 7, 2005).

Armenta et al., "Transesterification of Fish Oil to Produce Fatty Acid Ethyl Esters Using Ultrasonic Energy," J Am Oil Chem Soc. 84:1045-1052 (publication date: Nov. 2007, epublication date: Sep. 18, 2007).

Artero et al., "Fish Oil Metabolites: Translating Promising Findings From Bench to Bedside to Reduce Cardiovascular Disease," J Glycomics Lipidomics, 2(1):1000106 (publication date: Feb. 27, 2012).

Aveldaño et al., "Synthesis of hydroxy fatty acids from 4, 7, 10, 13, 16, 19-[1-14C] docosahexaenoic acid by human platelets," J Biol Chem 258(15):9339-43 (publication date: Aug. 10, 1983).

(Continued)

*Primary Examiner* — Leslie A. Royds Draper
(74) *Attorney, Agent, or Firm* — Perkins Coie LLP

(57) ABSTRACT

The present invention relates to a polyunsaturated fatty acid composition comprising Omega-3 fatty acids, 17-HDHA and 18-HEPE. The composition can furthermore comprise DPA and/or an acceptable carrier and can be present in a capsule or other suitable dosage unit. The invention also relates to the process of obtaining the composition and methods for using same.

18 Claims, 10 Drawing Sheets

(56) References Cited

OTHER PUBLICATIONS

Bannenberg et al., "Molecular circuits of resolution: formation and actions of resolvins and protectins," J. Immunol. 174(7):4345-55 (publication date: Apr. 1, 2005).
Bannenberg et al., "Specialized pro-resolving lipid mediators in the inflammatory response: An update," Biochim Biophys Acta. 1801(12):1260-73 (publication date: Dec. 2010, epublication date: Aug. 10, 2010).
Barden et al., "Specialised pro-resolving mediators of inflammation in inflammatory arthritis," Prostaglandins, Leukotrienes and Essential Fatty Acids 107:24-29 (publication date: Apr. 2016, epublication date: Mar. 9, 2016).
BASF Safety Data Sheet. "Omega Oil 1812 TG Gold," Revision Date Oct. 24, 2018, pp. 1-9 (2018).
Bento et al., "Omega-3 fatty acid-derived mediators 17(R)-hydroxy docosahexaenoic acid, aspirin-triggered resolvin D1 and resolvin D2 prevent experimental colitis in mice," Journal of Immunology, 187(4):1957-69. (publication date: Aug. 15, 2011, epublication date: Jul. 1, 2011).
Biswas et al., "Macrophage plasticity and interaction with lymphocyte subsets: cancer as a paradigm," Nature Immunol. 11, 889-896. (publication date: Oct. 2010, epublication date: Sep. 20, 2010).
Cao et al., "A specific role of integrin Mac-1 in accelerated macrophage efflux to the lymphatics," Blood. 106(9):3234-41. (publication date: Nov. 1, 2005, epublication date: Jul. 7, 2005).
Chiu et al., "Omega-6 docosapentaenoic acid-derived resolvins and 17-hydroxydocosahexaenoic acid modulate macrophage function and alleviate experimental colitis," Inflamm Res 61(9):967-76 (publication date: Sep. 2012, epublication date: May 23, 2012).
Clària et al., "Diversity of lipid mediators in human adipose tissue depots," Am J Physiol Cell Physiol 304(12):C1141-9 (publication date: Jun. 2013. epublication date: Jan. 30, 2013).
Clària et al., "Resolvin D1 and resolvin D2 govern local inflammatory tone in obese fat," J Immunol. 189(5):2597-605 (publication date: Sep. 1, 2012, Jul. 27, 2012).
Colas et al., "Identification and signature profiles for pro-resolving and inflammatory lipid mediators in human tissue," Am J Physiol Cell Physiol. 307(1):C39-54 (publication date: Jul. 1, 2014, epublication date: Apr. 2, 2014).
Cunningham, "Proinflammatory Properties of Unsaturated Fatty Acids and Their Monohydroxy Metabolites," Prostaglandins 30(3):498-509 (publication date: Sep. 1985).
Dallegri et al., "Tissue injury in neutrophilic inflammation," Inflamm Res. 46(10):382-391 (publication date: Oct. 1997) (Abstract only).
Dalli et al., "Novel n-3 Immunoresolvents: Structures and Actions," Scientific Reports 3. Article No. 1940 doi:10.1038/srep01940 (publication date: Jun. 5, 2013).
Dalli et al., "Resolvin D3 and Aspirin Triggered Resolvin D3 are Potent Immunoresolvents," Chem Biol. 20(2):188-201 (publication date: Feb. 21, 2013).
Dalli et al., "Specific lipid mediator signatures of human phagocytes: microparticles stimulate macrophage efferocytosis and pro-resolving mediators," Blood. 120(15):e60-e72 (publication date: Oct. 11, 2012, epublication date: Aug. 17, 2012).
Dangi et al., "Biogenic Synthesis, Purification, and Chemical Characterization of Anti-inflammatory Resolvins Derived from Docosapentaenoic Acid (DPAn-6)," Journal of Biological Chemistry, 284(22):14744-14759 (publication date: May 29, 2009, epublication date: Mar. 26, 2009).
Endo et al., "18-HEPE and n-3 fatty acid metabolite released by macrophages, prevents pressure overload-induced maladaptive cardiac remodeling," J Exp Med. 211(8):1673-87 (publication date: Jul. 28, 2014, epublication date: Jul. 21, 2014).
Fischer et al., "Uptake, release and metabolism of docosahexaenoic acid (DHA, c22:6 omega 3) in human platelets and neutrophils," Biochem Biophys Res Commun 120(3):907-18 (publication date: May 16, 1984).
Fogh et al., "Improvement of psoriasis vulgaris after intralesional injections of 15-hydroxyeicosatetraenoic acid (15-HETE)," J Am Acad Dermatol 18(Issue 2, Part 1):279-285 (publication date: Feb. 1988) (part of this study was published in a letter to the editor in Laneet in 1986).
Fredman et al., "Impaired phagocytosis in localized aggressive periodontitis: rescue by Resolvin E1," PLoS One 6(9):e24422 (epublication date: Sep. 14, 2011).
Gladyshev et al., "Production of EPA and DHA in aquatic ecosystems and their transfer to the land," Prostaglandins Other Lipid Mediat. 107:117-26 (publication date: Dec. 2013, epublication date: Mar. 14, 2013) (Abstract only).
Gleissman et al., "Docosahexaenoic acid metabolome in neural tumors: identification of cytotoxic intermediates," FASEB J 24(3):906-15 (publication date: Mar. 2010, epublication date: Nov. 4, 2009).
González-Périz et al., "Docosahexaenoic acid (DHA) blunts liver injury by conversion to protective lipid mediators: protectin D1 and 17S-hydroxy-DHA," (14):2537-9 (publication date: Dec. 2006, epublication date: Oct. 20, 2006).
Gordon, S., "Alternative activation of macrophages," Nat Rev Immunol. (1):23-35 (publication date: Jan. 2003) (Abstract only).
Gross et al., "Bioluminescence imaging of myeloperoxidase activity in vivo," Nat. Med. 15(4):455-61 (publication date: Apr. 2009, epublication date: Mar. 22, 2009).
Han et al., "Limiting inflammatory responses during activation of innate immunity," Nat. Immunol. 6(12):1198-1205 (publication date: Dec. 2005) (Abstract only).
Haraldsson et al., "Separation of Eicosapentaenoic Acid and Docosahexaenoic Acid in Fish Oil by Kinetic Resolution Using Lipase," J. Am. Oil Chem. Soc. 75:1551-1556 (publication date: Nov. 1998).
Haraldsson et al., "The Preparation of Concentrates of Eicosapentaenoic Acid and Docosahexaenoic Acid by Lipase-Catalyzed Transesterification of Fish Oil with Ethanol," J. Am. Oil Chem. Soc. 74(11):1419-1424 (publication date: Nov. 1997).
Haslett C., "Resolution of acute inflammation and the role of apoptosis in the tissue fate of granulocytes," Clin Sci (Lond). 83(6):639-48 (publication date: Dec. 1992).
Hawthorne et al., "High dose eicosapentaenoic acid ethyl ester: effects on lipids and neutrophil leukotriene production in normal volunteers," Br. J. Clin. Pharmac. 30(2):187-194 (publication date: Aug. 1990).
Hills et al., "Enzymatic Fractionation of Fatty Acids: Enrichment of γ-Linolenic Acid and Docosahexaenoic Acid by Selective Esterification Catalyzed by Lipases," J. Am. Oil Chem. Soc. 67(9):561-564 (publication date: Sep. 1990).
Hong et al., "Novel docosatrienes and 17S-resolvins generated from docosahexaenoic acid in murine brain, human blood, and glial cells," J Biol Chem. 278(17):14677-87 (publication date: Apr. 25, 2003, epublication date: Feb. 17, 2003).
Hong et al., "Rainbow trout (*Oncorhynchus mykiss*) brain cells biosynthesize novel docosahexaenoic acid-derived resolvins and protectins-Mediator Lipidomic analysis," Prostaglandins Other Lipid Mediat. 78(1-4):107-16 (publication date: Dec. 2005, epublication date: Jun. 13, 2005) (Abstract only).
Huynh et al., "Phosphatidylserine-dependent ingestion of apoptotic cells promotes TGF-β1 secretion and the resolution of inflammation," J Clin Invest. 109(1):41-50. (publication date: Jan. 1, 2002).
International Search Report and Written Opinion dated Dec. 2, 2016 for International Application No. PCT/US2016/050397.
International Search Report and Written Opinion dated Oct. 31, 2013 for International Application No. PCT/US2013/40314.
Isobe et al., "Identification and structure determination of novel anti-inflammatory mediator resolvin E3, 17,18-dihydroxyeicosapentaenoic acid," J Biol Chem, 287(13):10525-34 (publication date: Mar. 23, 2012).
Kadota et al., "Separation of Polyunsaturated Fatty Acids by Chromatography Using a Silver-Loaded Spherical Clay. I. Pilot-Scale Preparation of High purity Docosahexaenoic Acid by Supercritical Fluid Chromatography," Journal of Oleo Science 46(4):397-403 (1997) (with English translation).
Kohli et al., "Resolvins and protectins: mediating solutions to inflammation," Br. J. Pharmacol. 158(4):960-971 (publication date: Oct. 2009, epublication date: Jul. 7, 2009).

(56) References Cited

OTHER PUBLICATIONS

Köhnke et al., "Acetylsalicylic Acid Reduces the Severity of Dextran Sodium Sulfate-Induced Colitis and Increases the Formation of Anti-Inflammatory Lipid Mediators," Biomed Res Int. Article ID No. 748160 (epublication date: Sep. 8, 2013).

Kremer "n-3 Fatty acid supplements in rheumatoid arthritis," Am. J. Clin. Nutr. 71(suppl):349S-351S (publication date: Jan. 2000).

Krishnamurthy et al., "Total synthesis and bioactivity of 18(R)-hydroxyeicosapentaenoic acid," J Org Chem, 76(13):5433-7 (publication date: Jul. 1, 2011).

Kuo et al., "Anti-inflammatory Effects of Supercritical Carbon Dioxide Extract and Its Isolated Carnosic Acid from Rosmarinus officinalis Leaves," J. Agric. Food Chem. 59:3674-85 (publication date: Apr. 27, 2011, epublication date: Mar. 4, 2011).

Levy et al., "Lipid mediator class switching during acute inflammation: signals in resolution," Nat Immunol. 2(7):612-9 (publication date: Jul. 2001) (Abstract only).

Levy et al., "Resolution of acute inflammation in the lung," Annu. Rev. Physiol. 76:467-492 (epublication date: Dec. 2, 2013).

Lima-Garcia et al., "The precursor of resolvin D series and aspirin-triggered resolvin D1 display antihyperalgesic properties in adjuvant-induced arthritis in rats," Br J Pharmacol. 164(2):278-293 (publication date: Sep. 2011).

Lin et al., "Enrichment of n-3 PUFA contents on triglycerides of fish oil by trans-esterification under supercritical conditions," Biochemical Engineering Journal 29 (Issues 1-2):27-34 (Apr. 1, 2006) (epublication date: Jul. 11, 2005).

López-Vicario et al., "Inhibition of soluble epoxide hydrolase modulates inflammation and autophagy in obese adipose tissue and liver: role for Omega-3 epoxides," Proc Natl Acad Sci U S A. 112(2):536-41 (epublication date: Dec. 30, 2014).

Lovaza, Generic Name: omega-3-acid ethyl esters Brand Name: Lovaza, https://www.rxlist.com/lovaza-drug.htm.

Maehr et al., "Enzymic Enhancement of n-3 Fatty Acid Content in Fish Oils," J. Am. Oil Chem. Soc. 71(5):463-467 (May 1994) (This paper was presented at the 82nd AOCS Annual Meeting, May 12-15, 1991).

Mas et al., "Resolvins D1, D2, and other mediators of self-limited resolution of inflammation in human blood following n-3 fatty acid supplementation," Clinical Chemistry 58:10:1476-84 (publication date: Oct. 2012, epublication date: Aug. 21, 2012).

Masoodi et al., "Simultaneous lipidomic analysis of three families of bioactive lipid mediators leukotrienes, resolvins, protectins and related hydroxy-fatty acids by liquid chromatography/electrospray tandem mass spectrometry," Rapid Commun Mass Spectrom. 22(2):75-83 (publication date: Sep. 18, 2008).

McKimmie et al., "Leucocyte expression of the chemokine scavenger D6," Biochem Soc Trans. 34(Pt 6):1002-4 (publication date: Dec. 2006).

Metlay et al., "Time course of symptom resolution in patients with community-acquired pneumonia," Respir Med. 92(9):1137-42 (publication date: Sep. 1998).

Miller et al., "Dietary Supplementation with Ethyl Ester Concentrates of Fish Oil (n-3) and Borage Oil (n-6) Polyunsaturated Fatty Acids Induces Epidermal Generation of Local Putative Anti-Inflammatory Metabolites," J. Invest. Dermatol. 96(1):98-103 (Jan. 1991).

Miyahara et al., "D-series resolvins attenuate vascular smooth muscle cell activation and neointimal hyperplasia following vascular injury," FASEB J. 27:2220-2232 (publication date: Jun. 2013, epublication date: Feb. 13, 2013).

Murphy et al., "Fatty acid and sterol composition of frozen and freeze-dried New Zealand Green Lipped Mussel (*Perna canaliculus*) from three sites in New Zealand," Asia Pacific J. Clin. Nutr. 12(1):50-60 (publication date: Mar. 2003).

Nagakura et al., "Dietary supplementation with fish oil rich inomega-3 polyunsaturated fatty acids in children with bronchial asthma," Eur Respir J, 16(5):861-5 (publication date: Nov. 200).

Neuhofer et al., "Impaired local production of proresolving lipid mediators in obesity and 17-HDHA as a potential treatment for obesity-associated inflammation," 62(6):1945-56 (publication date: Jun. 2013, epublication date: Jan. 24, 2013).

Norling et al., "Cutting edge: Humanized nano-proresolving medicines mimic inflammation-resolution and enhance wound healing," J Immunol 6186(10):5543-7 (publication date: May 15, 2011, epublication date: Apr. 1, 2011).

Ogawa et al., "Total synthesis and bioactivity of resolvin E2," Org Lett, 11(16):3602-5 (publication date: Aug. 20, 2009).

Oh et al., "Chiral lipidomics of E-series resolvins: aspirin and the biosynthesis of novel mediators," Biochim Biophys Acta. 1811(11):737-47 (publication date: Nov. 2011, epublication date: Jun. 16, 2011).

Oh et al., "Pro-resolving actions and stereoselective biosynthesis of 18S E-series resolvins in human leukocytes and murine inflammation," J Clin Invest. 121(2):569-81 (publication date: Feb. 2011, epublication date: Jan. 4, 2011).

Oh et al., "Resolvin E2: formation and impact in inflammation resolution," J Immunol. 188(9):4527-34 (publication date: May 1, 2012, epublication date: Mar. 26, 2012).

Ohira et al., "Resolvin E1 receptor activation signals phosphorylation and phagocytosis," J. Biol. Chem. 285(5):3451-61 (publication date: Jan. 29, 2010, epublication date: Nov. 11, 2009).

Paragraphs 13, 14 and 51 of the *Transcript* which accompanies Documento di Ammsisione (Pharmanutra) online at https://docplayer.it/54881332-Documento-di-ammissione.html#show_full_text. (with English translation).

Perretti et al., "Supercritical carbon dioxide fractionation of fish oil fatty acid ethyl esters," J. of Supercritical Fluids 40:349-353 (publication date: Apr. 2007, epublication date: Aug. 30, 2006).

Petrie et al., "Metabolic engineering plant seeds with fish oil-like levels of DHA," PLoS One. 7(11):e49165 (epublication date: Nov. 7, 2012).

Pettitt et al., "Lipoxins are major lipoxygenase products of rainbow trout macrophages," FEBS Lett 259(1):168-70 (publication date: Dec. 18, 1989) (Abstract only).

Psychogios et al., "The human serum metabolome," PLoS ONE. 6(2):e16957 (publication date: Feb. 16, 2011).

Raatz et al., "Baking reduces prostaglandin, resolvin, and hydroxy-fatty acid content of farm-raised Atlantic salmon (*Salmo salar*)," J Agric Food Chem 59(20):11278-86 (epublication date: Oct. 4, 2011).

Ramon et al., "Specialized proresolving mediators enhance human B cell differentiation to antibody-secreting cells," J Immunol 189(2):1036-42 (publication date: Jul. 15, 2012, epublication date: Jun. 18, 2012).

Ramon et al., "The specialized proresolving mediator 17-HDHA enhances the antibody-mediated immune response against influenza virus: a new class of adjuvant?," J Immunol. 193(12):6031-40 (publication date: Dec. 15, 2014, epublication date: Nov. 12, 2014).

Rhodes et al., "The sunburn response in human skin is characterized by sequential eicosanoid profiles that may mediate its early and late phases," FASAB J. 23(11):3947-56 (publication date: Nov. 2009, epublication date: Jul. 7, 2009).

Sales, "Fish oil: The quintessential fatty acid Fish Oil consumption reduces illness and effects of aging," Argo Food Industry Hi-Tech, 22(1):30-32 (publication date: Jan. 2011).

Sapieha et al., "5-Lipoxygenase metabolite 4-HDHA is a mediator of the antiangiogenic effect of ω-3 polyunsaturated fatty acids," Sci Transl Med 3(69):69ra12 (publication date: Feb. 9, 2011).

Savill et al., "Granulocyte clearance by apoptosis in the resolution of inflammation," Semin Cell Biol. 6(6):385-93 (publication date: Dec. 1995) (Abstract only).

Sawazaki et al., "Lipoxygenation of docosahexaenoic acid by the rat pineal body," J Neurochem 62(6):2437-47 (publication date: Jun. 1994).

Schwab et al., "Resolvin E1 and protectin D1 activate inflammation-resolution programs," Nature. 447:869-74 (publication date: Jun. 14, 2007).

Serhan et al., "Endogenous pro-resolving and anti-inflammatory lipid mediators: A new pharmacologic genus," Br J Pharmacol 153:S200-15 (publication date: Mar. 2008, egublication date: Oct. 29, 2007).

(56) References Cited

OTHER PUBLICATIONS

Serhan et al., "Lipoxins: novel series of biologically active compounds formed from arachidonic acid in human leukocytes," Proc Nati Acad Sci USA, 81(17):5335-39 (publication date: Sep. 1984).
Serhan et al., "Novel functional sets of lipid-derived mediators with antiinflammatory actions generated from omega-3 fatty acids via cyclooxygenase 2-nonsteroidal antiinflammatory drugs and transcellular processing," J Exp Med. 192(8):1197-204 (publication date: Oct. 16, 2000).
Serhan et al., "Resolution of inflammation: the beginning programs the end," Nat Immunol. 6(12):1191-97 (publication date: Dec. 2005) (Abstract only).
Serhan et al., "Resolution phase lipid mediators of inflammation: agonists of resolution," Curr Opin Pharmacol. 13(4):632-40 (publication date: Aug. 13, 2013, epublication date: Jun. 6, 2013).
Serhan et al., "Resolving inflammation: dual anti-inflammatory and pro-resolution lipid mediators," Nat Rev Immunol. 8(5):349-61. (publication date: May 2008).
Serhan et al., "Resolvins and Protectins in Inflammation Resolution," Chemical Reviews, 111:5922-5943 (publication date: Oct. 12, 2011, epublication date: Jul. 18, 2011).
Serhan et al., "Resolvins: a family of bioactive products of Omega-3 fatty acid transformation circuits initiated by aspirin treatment that counter proinflammation signals," J Exp Med. 196(8)1 025-37 (publication date: Oct. 21, 2002).
Serhan et al., "Resolvins and Protectins in Inflammation-Resolution," Chem Rev. 111(10):5922-43 (publication date: Oct. 12, 2011, epublication date: Jul. 18, 2011).
Serhan, "Novel eicosanoid and docosanoid mediators: Resolvins, docosatrienes, and neuroprotectins," Curr Opin Clin Nutr Metab Care. 8(2):115-21 (publication date: Mar. 2005).
Serhan, "Novel pro-resolving lipid mediators are leads for resolution physiology," Nature. 510(7503):92-101 (publication date: Jun. 5, 2014).
Shaikh et al., "n-3 Polyunsaturated fatty acids exert immunomodulatory effects on lymphocytes by targeting plasma membrane molecular organization," Mol Aspects Med,33(1):46-54 (epublication date: Oct. 19, 2011).
Shearer et al., "Detection of omega-3 oxylipins in human plasma and response to treatment with omega-3 acid ethyl esters," J Lipid Res 51(8):2074-2081 (publication date: Aug. 2010, epublication date: Aug. 11, 2009).
Singer et al., "Anti-inflammatory properties of omega-3 fatty acids in critical illness: novel mechanisms and an integrative perspective," Intensive Care Med. 34:1580-92 (publication date: Sep. 2008, epublication date: May 7, 2008).
Spite et al., "Novel lipid mediators promote resolution of acute inflammation: Impact of aspirin and statins," Cir Res 107(10):1170-84 (publication date: Nov. 12, 2010).
Spite et al., "Resolvins, specialized proresolving lipid mediators, and their potential roles in metabolic diseases," Cell Metab 19(1):21-36 (publication date: Jan. 7, 2014, epublication date: Nov. 14, 2013).
Stuart et al., "Apoptotic cells and innate immune stimuli combine to regulate macrophage cytokine secretion," J Immunol. 171(5):2610-15 (publication date: Sep. 1, 2003).
Sun et al., "Resolvin D1 and its aspirin-triggered 17R epimer: stereochemical assignments, anti-inflammatory properties, and enzymatic inactivation," J Biol Chem. 282(13):9323-34 (publication date: Mar. 30, 2007, epublication date: Jan. 23, 2007).
Tabas et al., "Anti-inflammatory therapy in chronic disease: challenges and opportunities," Science. 339(6116):166-72 (Jan. 11, 2013).
Ternowitz et al., "15-Hydroxyeicosatetraenoic acid (15-HETE) specifically inhibits LTB4-induced chemotaxis of human neutrophils," Skin Pharmacol 1(2):93-9 (1988).
Ternowitz et al., "15-Hydroxyeicosatetraenoic acid (15-HETE) specifically inhibits the LTB4-induced skin response," Arch Dermatol Res (281:401-405 (1989).
Titos et al., "Resolvin D1 and its precursor docosahexaenoic acid promote resolution of adipose tissue inflammation by eliciting macrophage polarization toward an M2-like phenotype," J Immunol. 187(10):5408-18 (publication date: Nov. 15, 2011, epublication date: Oct. 17, 2011).
Uddin et al., "Resolvins: Natural agonists for resolution of pulmonary inflammation," Progress in Lipid Research. 50:75-88 (publication date: Jan. 2011, epublication date: Sep. 29, 2010).
Uller et al., "Resolution of airway disease: removal of inflammatory cells through apoptosis, egression or both?" Trends Pharmacol Sci. 27(9):461-6 (publication date: Sep. 2006, epublication date: Jul. 31, 2006) (Abstract only).
VanRollins et al., "Oxidation of docosahexaenoic acid by rat liver microsomes," J Biol Chem 259(9):5776-83 (publication date: May 10, 1984).
Varani et al., "Mechanisms of endothelial cell injury in acute inflammation," Shock. 2(5):311-9 (publication date: Nov. 1994) (Abstract only).
Wagner et al., "Soluble epoxide hydrolase inhibition, epoxygenated fatty acids and nociception," Prostaglandins Other Lipid Mediat. 96(1-4):76-83 (publication date: Nov. 2011, epublication date: Aug. 10, 2011).
Walker et al., "Regulation of neutrophil apoptosis and removal of apoptotic cells," Curr Drug Targets Inflamm Allergy. 4(4):447-54 (publication date: Aug. 2005) (Abstract only).
Wang et al., "A process for the synthesis of PUFA-enriched triglycerides from high-acid crude fish oil," J. Food Engineering 109:366-71 (epublication date: Nov. 25, 2011).
Wang et al., "Hydroxyeicosapentaenoic acids and epoxyeicosatetraenoic acids attenuate early occurance of nonalcoholic fatty liver disease," British Journal of Pharmacology, 174:2358-72 (epublication date: Jun. 9, 2017).
Weiss, "Tissue destruction by neutrophils," N Engl J Med 320(6):365-76 (publication date: Feb. 9, 1989) (Abstract only).
Weitz et al., "Fish Oil for the Treatment of Cardiovascular Disease," Cardiol Rev. 15(5):258-63 (publication date: Sep.-Oct. 2010).
Weylandt et al., "Lipoxins and resolvins in inflammatory bowel disease," Inflammatory Bowel Diseases. 13(6):797-9 (publication date: Jun. 2007) (Abstract only).
Weylandt et al., "Omega-3 fatty acids and their lipid mediators: towards an understanding of resolvin and protectin formation," Prostaglandins Other Lipid Mediat 97(3-4):73-82 (publication date: Mar. 2012, epublication date: Feb. 3, 2012).
Weylandt et al., "Suppressed liver tumorigenesis in fat-1 mice with elevated omega-3 fatty acids is associated with increased omega-3 derived lipid mediators and reduced TNF-α," Carcinogenesis. 32(6):897-903 (publication date: Jun. 2011, epublication date: Mar. 17, 2011).
White et al., "Resolution of bronchial inflammation is related to bacterial eradication following treatment of exacerbations of chronic bronchitis," Thorax. 58(8):680-85 (publication date: Aug. 2003).
Willoughby et al., "Resolution of inflammation," Intl J Immunopharmacol. 22(12):1131-5 (publication date: Dec. 2000) (Abstract only).
Yamamoto et al., "4-Hydroxydocosahexaenoic acid, a potent peroxisome proliferator-activated receptor gamma agonist alleviates the symptoms of DSS-induced colitis," Biochem Biophys Res Commun 367(3):566-72 (publication date: Mar. 14, 2008, epublication date: Jan. 10, 2008).
Yang et al., "Metabolomics-lipidomics of eicosanoids and docosanoids generated by phagocytes," Curr Protoc Immunol. Chapter 14, Unit 14 (publication date: Nov. 2011) (Abstract only).
Frequently Asked Questions About Medical Foods; Second Edition, Guidance for Industry, U.S. Department of Health and Human Services Food and Drug Administration Center for Food Safety and Applied Nutrition May 2016.
Mori et al., "Interactions Between Dietary Fat, Fish, and Fish Oils and Their Effects on Platelet Function in Men at Risk of Cardiovascular Disease," Artheriosclerosis, Thrombosis and Vascular Biology, 17(2):279-286 ( publication date: Feb. 1997).
Raskin et al., "Can an Apple a Day Keep the Doctor Away?" Current Pharmaceutical Design, 10:3419-3429 (2004).
Revilla et al., "Comparison of Several Procedures Used for the Extraction of Anthocyanins from Red Grapes," J. Agric, Food Chem. 46:4592-4597 (epublication date: Oct. 29, 1998).

(56) References Cited

OTHER PUBLICATIONS

Wu et al., "Effect of Concomitant Consumption of Fish Oil and Vitamin E on Production of Inflammatory Cytokines in Healthy Elderly Humans," Ann. N.Y. Acad. Sci. 1031:422-424 (2004).

COMPOSITIONS COMPRISING OMEGA-3 FATTY ACIDS, 17-HDHA AND 18-HEPE AND METHODS OF USING SAME

PRIORITY CLAIM

This application is a continuation of U.S. patent application Ser. No. 16/843,416, filed Apr. 8, 2020, which is a continuation of U.S. patent application Ser. No. 15/757,023, filed Mar. 2, 2018, which is a 35 USC § 371 U.S. National Stage Application of International Patent Application No. PCT/US2016/050397, filed Sep. 6, 2016, which claims priority to U.S. Provisional Application No. 62/213,958, filed Sep. 3, 2015, the entirety of each which is hereby incorporated by reference herein.

TECHNICAL FIELD

The present disclosure relates to a polyunsaturated fatty acid composition comprising 17-HDHA and 18-HEPE among other Omega-3 fatty acids. The compositions can furthermore comprise DPA and/or an acceptable carrier and can be present in a capsule or other suitable dosage unit. Processes of obtaining and using the compositions are also provided.

BACKGROUND

Inflammation is an unspecific response in defense of external pathogen agents to eliminate them and repair damaged tissues. Inflammation is a complex physiologic process that could be considered as acute or chronic depending on the duration of this process.

Chronic inflammation is maintained over time, as a result of a lack of resolution of the acute initial phase of the inflammatory response or progressive initiation associated with diseases such as rheumatoid arthritis, atherosclerosis, tuberculosis, cancer, vascular diseases, metabolic syndrome, and neurological diseases as Alzheimer among others.

Resolution of the inflammation is a different process from the anti-inflammatory process. Resolution of inflammation can be defined as the interval between maximum neutrophil infiltration to the point when they are lost from the tissue. Complete resolution is the ideal outcome of inflammation, although, if not properly regulated, it can lead to chronic inflammation, fibrosis, and loss of function.

Pathologists divide the inflammatory response into initiation and resolution. The natural mechanism of the resolution of inflammation has acquired a high relevance during the last years due to the inflammation being recognized as an important characteristic of the above diseases. Resolution was considered to be a passive process before the discovery and identification of specialized pro-resolving mediators.

Effective clearance of microbial infections and damaged tissue is self-limited and followed by resolution of inflammation. Resolution can be defined at the cellular level as the disappearance of accumulated polymorphonuclear leukocytes, and at the macroscopic level as reconstitution of tissue architecture and restoration of normal function. Complete restoration of tissue integrity after bacterial infection is directly related to the efficiency of microbe clearance and then to leukocyte clearance. Several mechanisms appear to drive the disappearance of inflammatory leukocytes. Apoptosis of leukocytes is one important route of elimination. Once phagocytosis is complete, leukocytes undergo programmed cell deaths in response to locally released mediators which regulate the rate of apoptosis. As polymorphonuclear leukocytes die, they simultaneously function as cytokine sinks and sequester earlier released pro-inflammatory cytokines. Apoptotic neutrophils are subsequently phagocytozed by macrophages (efferocytosis) in a so-called non-phlogistic fashion (i.e., in the absence of further generation of pro-inflammatory mediators), but with increased formation of anti-inflammatory mediators such as transforming growth factor-β (TGF-β), lipoxin A4 (LXA4) and interleukin-10. Another important route of elimination of leukocytes is egress from the inflamed tissue, as shown for eosinophils in pulmonary inflammation. Macrophages which have eliminated apoptotic neutrophils disappear in turn by either apoptosis or egress via the lymphatic system as inflammation resolves.

Development of new products to facilitate the resolution of the inflammation, especially in chronic diseases associated with an important inflammatory component, such as Crohn's disease, irritable bowel disease (IBD), fatty liver, wound healing, arterial inflammation, sickle-cell disease, arthritis, psoriasis, urticaria, vasculitis, asthma, ocular inflammation, pulmonary inflammation, dermatitis, cardiovascular diseases, AIDS, Alzheimer's disease, atherosclerosis, cancer, type 2 diabetes, hypertension, infectious diseases, leukemia/lymphoma, metabolic syndrome, neonatology, neuromuscular disorders, obesity, perinatal disorders, rheumatic diseases, stroke, surgical transplantation, vascular disorders, periodontal diseases, brain injury, trauma and neuronal inflammation, among others, is greatly needed.

SUMMARY

In several embodiments, the present disclosure provides a polyunsaturated fatty acid composition comprising about 20% to about 95%, by weight, Omega-3 fatty acids, and 17-HDHA and 18-HEPE in a total amount of about 0.0005% to about 1% by weight of the composition. In some embodiments, the composition can further comprise DPA and/or an acceptable carrier and can be present in a capsule or other suitable dosage unit.

In one embodiment, the present disclosure provides a polyunsaturated fatty acid composition comprising about 20% to about 95%, by weight, Omega-3 fatty acids, and a collective amount of about 0.0005% to about 1% of 17-HDHA and 18-HEPE, by weight.

In another embodiment, the present disclosure provides a dietary supplement, pharmaceutical product, nutraceutical product, medical food, infant formulae and/or prenatal formulae composition comprising a composition as disclosed herein.

In another embodiment, the present disclosure provides a process for obtaining a composition as disclosed herein from an oil using a method selected from chromatography, extraction, distillation and/or vacuum rectification.

In another embodiment, the present disclosure provides a process for obtaining a composition as disclosed herein from a crude oil, the process comprising: (i) chemically esterifying crude oil with ethanol and a basic catalyst, at a temperature of about 55° C. to about 75° C. to produce esterified oil, (ii) distilling the esterified oil under vacuum of about 0.01 mbar to 0.6 mbar and at a temperature of about 130° C. to 190° C. for about 10 seconds to about 5 minutes to separate fatty acids shorter than 20 carbon atoms to obtain a distilled esterified oil comprising about 20% to about 95% by weight EPA and/or DHA, and about 0.0005% to about 1% by weight 17-HDHA and 18-HEPE (collectively); and (iii) subjecting the polyunsaturated fatty acid composition obtained in step (ii) to supercritical fluid extraction with $CO_2$ as a supercritical fluid at a temperature of about 39° C. to about 46° C. and pressure of about 80 bar to about 115 bar to remove oxidation, decomposition and/or degradation products as oligomers, dimers, polymers and conjugated dienes from the composition.

In another embodiment, the present disclosure provides a process for obtaining a composition as disclosed herein from a concentrated esterified oil, the process comprising: (i) distilling the concentrated esterified oil under vacuum of about 0.01 mbar to 0.6 mbar and at a temperature of about 130° C. to 190° C. for about 10 seconds to about 5 minutes to separate fatty acids having fewer than 20 carbon atoms in the corresponding fatty acid chain to obtain a distilled esterified oil comprising about 20% to about 95% by weight EPA and/or DHA, and about 0.0005% to about 1% by weight 17-HDHA and 18-HEPE (collectively); (ii) subjecting the distilled esterified oil obtained in step (i) to supercritical fluid extraction with $CO_2$ as a supercritical fluid at a temperature of about 20° C. to 40° C. and at a pressure of about 80 bar to about 115 bar to remove oxidation, decomposition and degradation products as oligomers, dimers, polymers and conjugated dienes from the composition.

In another embodiment, the present disclosure provides a method of increasing phagocytic activity of macrophages in a subject comprising administering to the subject a phagocytic activity enhancing amount of a composition as disclosed herein.

In another embodiment, the present disclosure provides a method of enhancing macrophage polarization toward a pro-resolution phenotype in a subject comprising administering to the subject a macrophage polarization-enhancing amount of a composition as disclosed herein.

In another embodiment, the present disclosure provides a method of resolving inflammation associated with a disease in a subject in need thereof comprising administering to the subject an inflammation-resolving amount of a composition as disclosed herein.

In another embodiment, the present disclosure provides a method of elevating SPM levels in plasma of a human subject comprising administering to the human subject an SPM-elevating amount of a composition as disclosed herein.

In another embodiment, the present disclosure provides use of a composition as disclosed herein as a vaccine coadjuvant.

In another embodiment, the present disclosure provides use of a composition as disclosed herein as a chemotherapeutic coadjuvant.

In another embodiment, the present disclosure provides use of a composition as disclosed herein in the manufacture of a medicament for increasing phagocytic activity of macrophages in a subject.

In another embodiment, the present disclosure provides use of a composition as disclosed herein in the manufacture of a medicament for enhancing macrophage polarization toward a pro-resolution phenotype in a subject.

In another embodiment, the present disclosure provides use of a composition as disclosed herein in the manufacture of a medicament for resolving inflammation associated with a disease in a subject in need thereof.

In another embodiment, the present disclosure provides use of a composition as disclosed herein in the manufacture of a medicament for elevating SPM levels in plasma of a human subject.

DETAILED DESCRIPTION

Figure 1A:
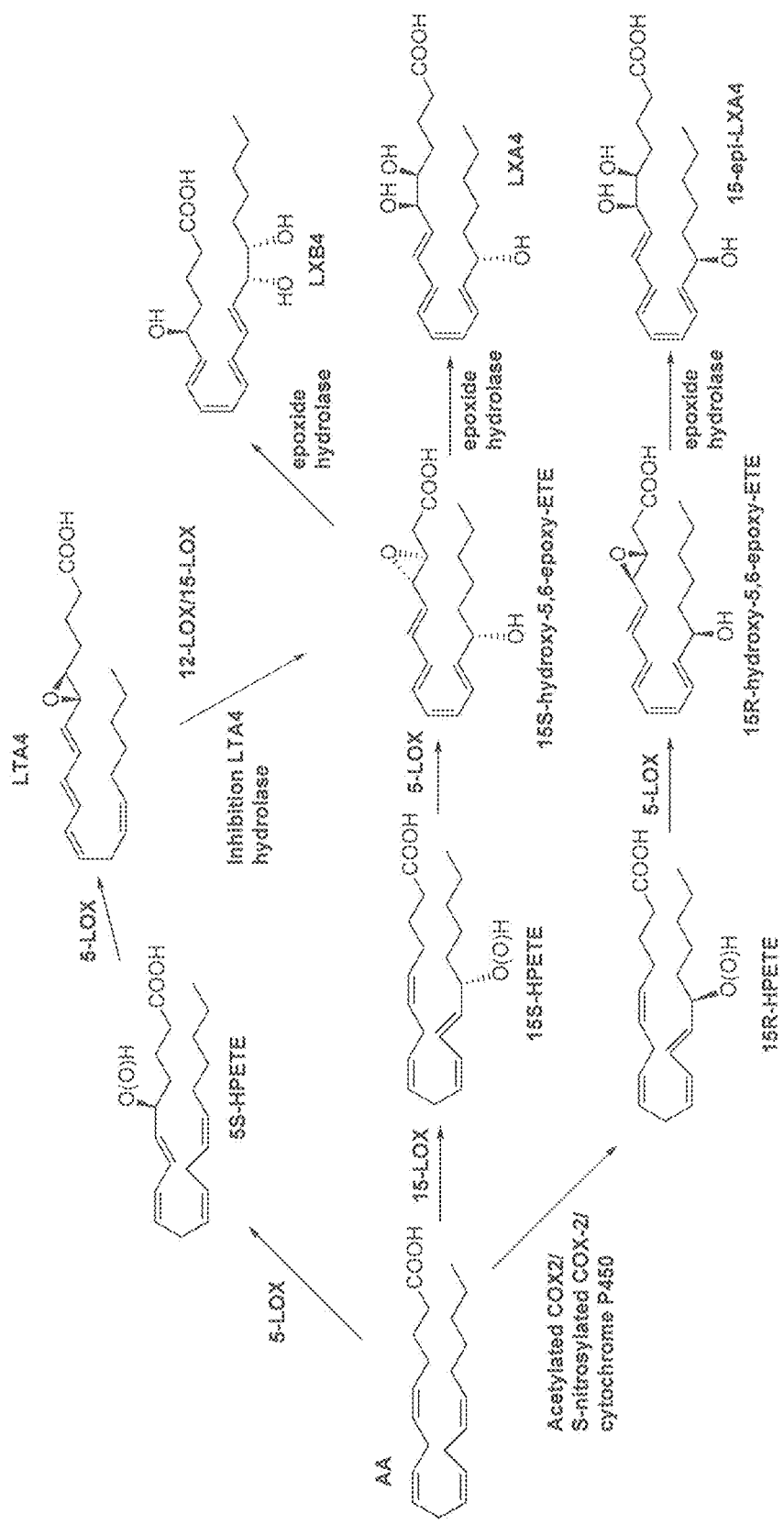
FIG. 1A: Biosynthesis of lipoxins and aspirin-triggered lipoxins from arachidonic acid.
Figure 1B:
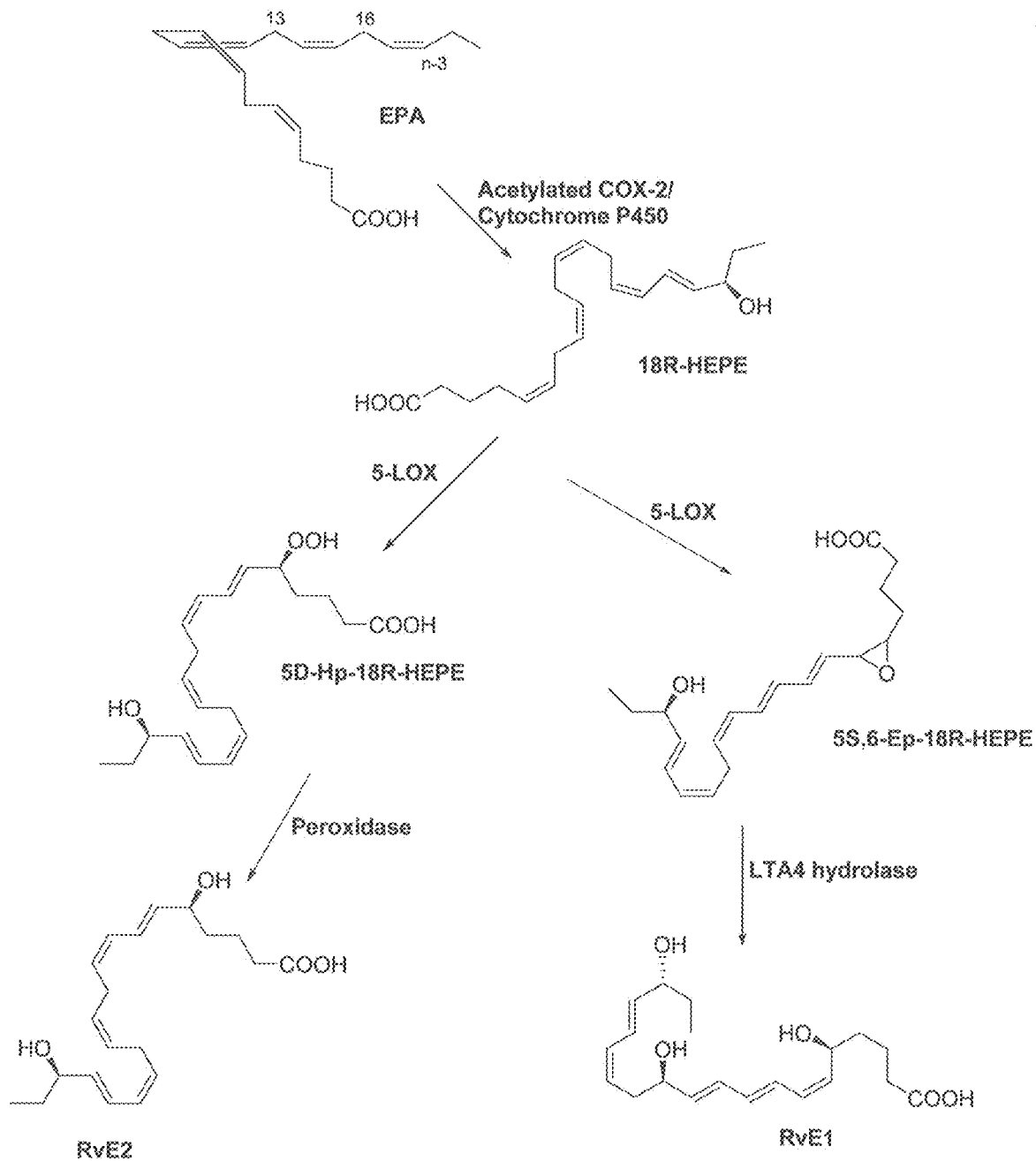
FIG. 1B: Biosynthesis of E-series resolvins: RvE1 and RvE2 from EPA.
Figure 1C:
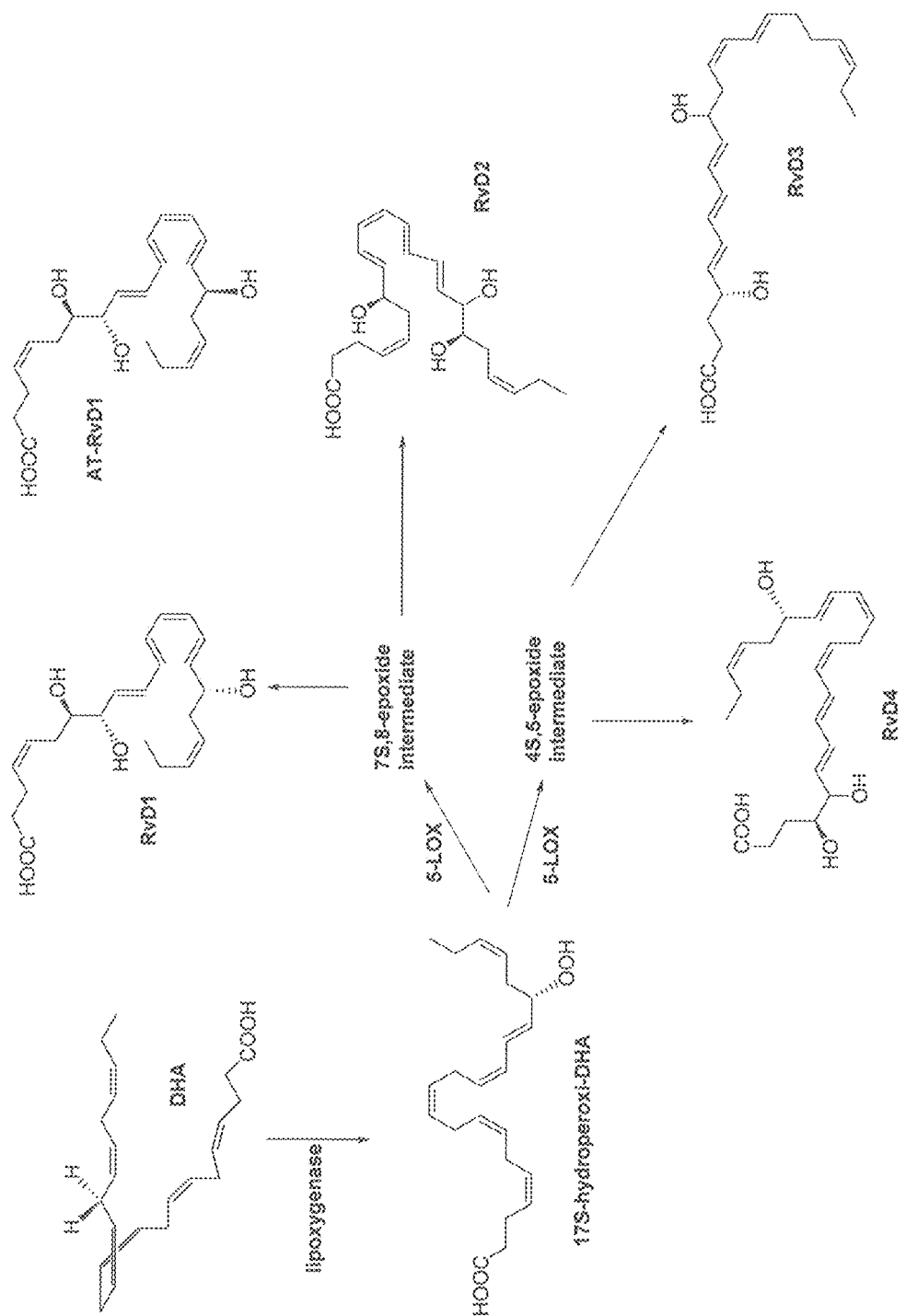
FIG. 1C: Biosynthesis of D series resolvins and aspirin-triggered D series resolvins.
Figure 1D:
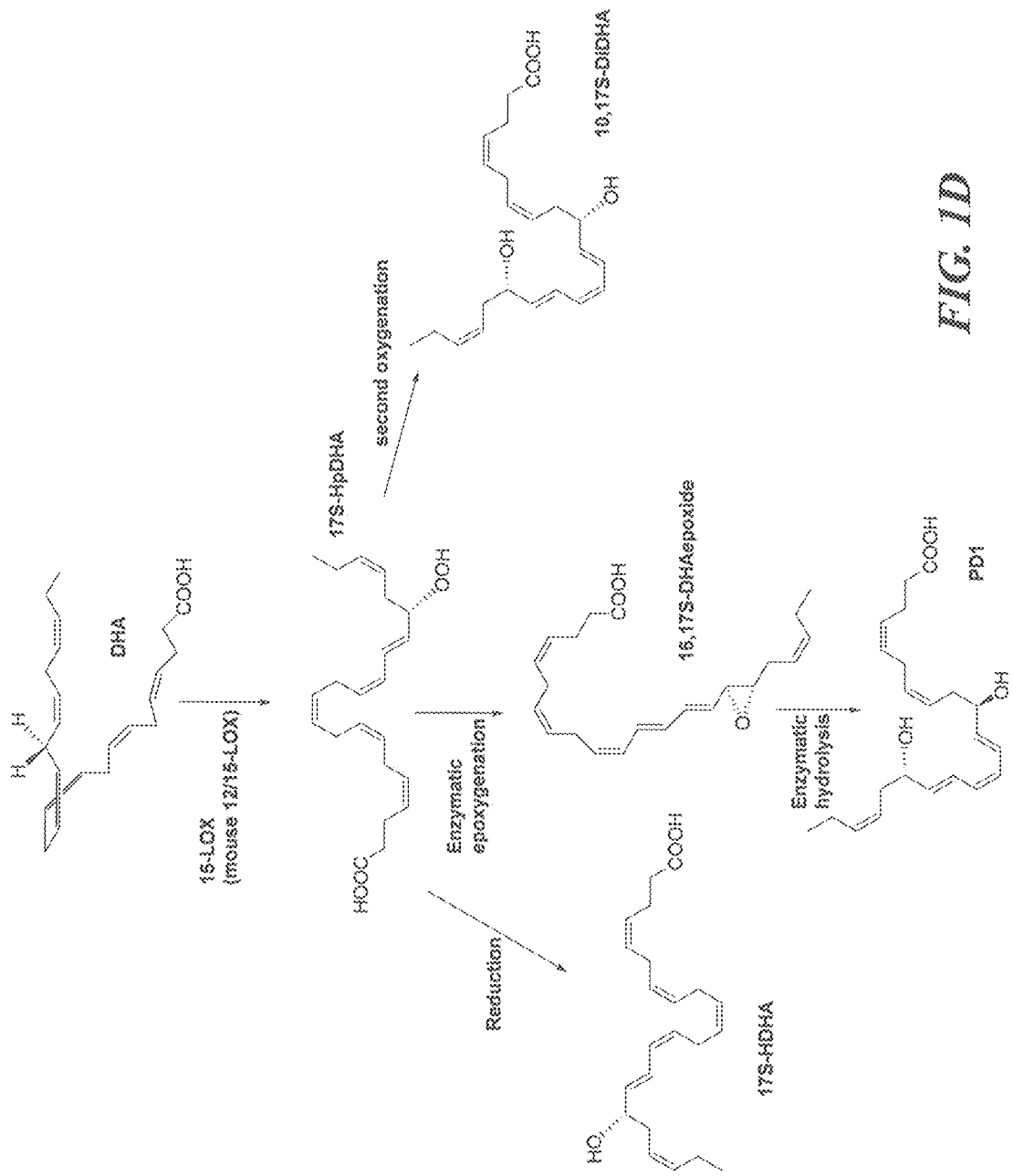
FIG. 1D: Biosynthesis of protectins: PD1 (the mono-hydroxylated product 17S-hydroxy-DHA), the mono-hydroxylated product 17S-hydroxy-DHA, and the double oxygenation product 10S,17S-dihydroxy-DHA, an isomer of NPD1/PD1.
Figure 1E:
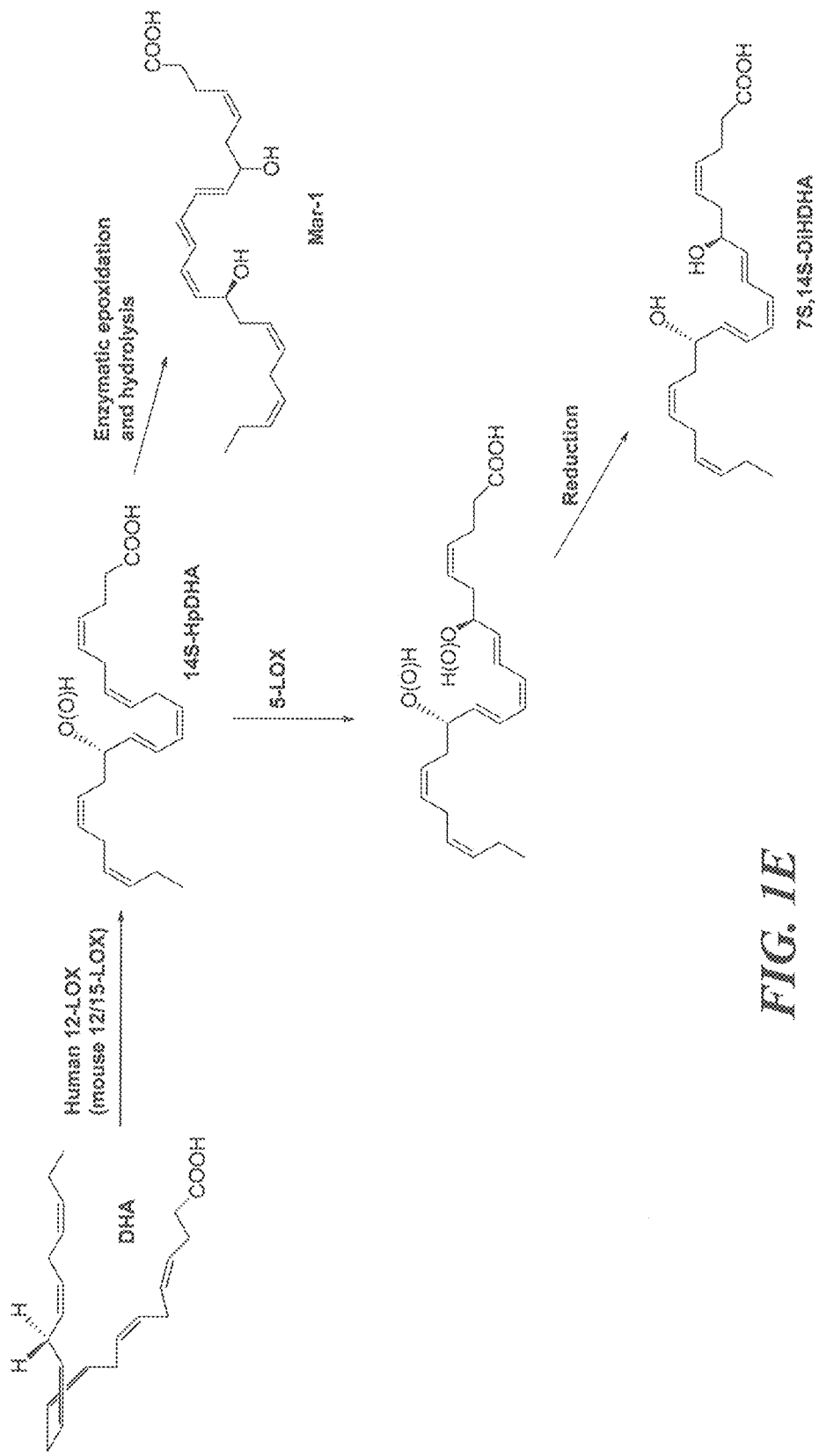
FIG. 1E: Formation of maresins: Mar-1 (7,14S-dihydroxy-DHA); also, an isomer 7S,14S-dihydroxy-DHA, a novel double dioxygenation product from this biosynthetic pathway.

The use of numerical values specified in this application, unless expressly indicated otherwise, are stated as approximations through the minimum and maximum values specified within the stated ranges, and preceded by the word "about." The disclosure of ranges is intended as a continuous range including every value between the minimum and maximum values recited as well as any ranges that can be formed through such values. The numerical values presented in this application represent various embodiments of the present invention.

In various embodiments, the present invention provides a polyunsaturated fatty acid composition comprising about 20% to about 95%, by weight, of Omega-3 fatty acids and about 0.0005% to about 1%17-HDHA and 18-HEPE (collectively) by weight of the composition.

Omega-3 fatty acids are a family of polyunsaturated fatty acids considered as essential fatty acids, because they cannot be synthesized by mammals. The main components of this family are EPA (5Z,8Z,11Z,14Z,17Z eicosapentaenoic acid), DHA (4Z,7Z,10Z,13Z,16Z,19Z docosahexaenoic acid), and ALA (9Z,12Z,15Z octadecatrienoic acid).

Other important components of the family of omega-3 fatty acids are n-3 DPA (7Z,10Z,13Z,16Z,19Z-docosapentaenoic acid). The compound n-3 DPA is an elongated metabolite/intermediate of EPA and an intermediate product between EPA and DHA.

In various embodiments, the Omega-3 fatty acids in the composition comprise EPA and/or DHA in an amount between about 20% to about 95% by weight of the composition.

In various embodiments, the Omega-3 fatty acids in the composition comprise EPA in an amount between about 20% to about 95% by weight of the composition.

In various embodiments, the Omega-3 fatty acids in the composition comprise DHA in an amount between about 20% to about 95% by weight of the composition.

In various embodiments, the composition comprises EPA in an amount between about 10% to about 26% by weight and DHA in an amount of about 30% to about 45% by weight of the composition.

SPMs are a new genus with several families of potent endogenous bioactive products derived from precursors essential fatty acids EPA, DHA, ARA and DPA that are biosynthesized by positional and stereospecific incorporation of one, two or three molecules of molecular oxygen into a polyunsaturated fatty acid using EPA, DHA, ALA and DPA as substrates into a catalyzed reaction involving fatty acid lipoxygenases, cyclooxygenase type-2, when acetylated by aspirin, and several cytochrome P450 oxidases.

The SPMs include several families of mediators, lipoxins, resolvins, protectins and maresins. Specific potent members of these families include among others:

Lipoxin A4: LXA4; 5S,6R,15S-trihydroxy-7E,9E,11Z,13E-eicosatetraenoic acid
15-epi-lipoxin A4: 15-epi-LXA4; (5S,6R,7E,9E,11Z,13E,15R)-5,6,15-trihydroxyicosa-7,9,11,13-tetraenoic acid
Lipoxin B4: LXB4; 5S,14R,15S-trihydroxy-6E,8Z,10E,12E-eicosatetraenoic acid
15-epi-lipoxin B4: 15-epi-LXB4; 5S,14R,15R-trihydroxy-6E,8Z,10E,12E-eicosatetraenoic acid
Resolvin E1: RvE1; 5S,12R,18R-trihydroxy-6Z,8E,10E,14Z,16E-eicosapentaenoic acid
18S-Resolvin E1: 18S-RvE1; 5S,12R,18S-trihydroxy-6Z,8E,10E,14Z,16E-eicosapentaenoic acid
20-hydroxy-Resolvin E1: 20-hydroxy-RvE1; 5S,12R,18S,20-tetrahydroxy-6Z,8E,10E,14Z,16E-eicosapentaenoic acid
Resolvin E2: RvE2; 5S,18R-dihydroxy-6E,8Z,11Z,14Z,16E-eicosapentaenoic acid
18S-Resolvin E2: 18S-RvE2; 5S,18S-dihydroxy-6E,8Z,11Z,14Z,16E-eicosapentaenoic acid
18S-Resolvin E3: 18S-RvE3; 17R,18S-dihydroxy-5Z,8Z,11Z,13E,15E-eicosapentaenoic acid
18R-Resolvin E3: 18R-RvE3; 17R,18R-dihydroxy-5Z,8Z,11Z,13E,15E-eicosapentaenoic acid
Maresin 1: MaR1; 7R,14S-dihydroxy-4Z,8E,10E,12E,16Z,19Z-docosahexaenoic acid
7S-Maresin 1: 7S-MaR1; 7S,14S-dihydroxy-4Z,8E,10E,12Z,16Z,19Z-docosahexaenoic acid
13R,14S-Maresin 2: 13R,14S-MaR2; 13R,14S-dihydroxy-4Z,7Z,9E,11E,16Z,19Z-hexaenoic acid
14S-hydroperoxy-4Z,7Z,10Z,12E,16Z,19Z-docosahexaenoic acid
Protectin DX: PDX; 10S,17S-dihydroxy-4Z,7Z,11E,13Z,15E,19Z-docosahexaenoic acid
14S, 21R-diHDHA: 14S,21R-dihydroxy-4Z,7Z,10Z,12E,16Z,19Z-docosahexaenoic acid
14R,21S-diHDHA: 14R,21S-dihydroxy-4Z,7Z,10Z,12E,16Z,19Z-docosahexaenoic acid
14R,21R-diHDHA: 14R,21R-dihydroxy-4Z,7Z,10Z,12E,16Z,19Z-docosahexaenoic acid
14S, 21S-diHDHA: 14S,21S-dihydroxy-4Z,7Z,10Z,12E,16Z,19Z-docosahexaenoic acid
16,17-diHDHA: 16,17-dihydroxy-4Z,7Z,10Z,12E,14E,19Z-docosahexaenoic acid
16,17-Epoxy-DHA: 16,17-Epoxy-4Z,7Z,10Z,12E,14E,19Z-docosahexaenoic acid
17S-HDHA: 17S-hydroxy-4Z,7Z,10Z,13Z,15E,19Z-docosahexaenoic acid
7,8-epoxy-17S-HDHA: 17S-hydroxy-4Z,7Z,10Z,13Z,15E,19Z-docosahexaenoic acid
Protectin D1: PD1; 10R,17S-dihydroxy-4Z,7Z,11E,13E,15Z,19Z-docosahexaenoic acid
10S,17S-HDHA: 10S,17S-dihydroxy-4Z,7Z,11E,13Z,15E,19Z-docosahexaenoic acid
16,17S-diHDHA: 16,17S-dihydroxy-4Z,7Z,10Z,12E,14E,19Z-docosahexaenoic acid
16,17-Epoxy-DHA: 16,17-Epoxy-4Z,7Z,10Z,12E,14E,19Z-docosahexaenoic acid
Resolvin D1: RvD1; 7S,8R,17S-trihydroxy-docosa-4Z,9E,11E,13Z,15E,19Z-hexaenoic acid
Resolvin D2: RvD2; 7S,16R,17S-trihydroxy-docosa-4Z,8E,10Z,12E,14E,19Z-hexaenoic acid
Resolvin D3: RvD3; 4S,11,17S-trihydroxy-5E,7E,9E,13Z,15E,19Z-docosahexaenoic acid
Resolvin D4: RvD4; 4S,5,17S-trihydroxy-6E,8E,10E,13E,15Z,19Z-docosahexaenoic acid
Resolvin D5: RvD5; 7S,17S-dihydroxy-5Z,8E,10Z,13Z,15E,19Z-docosahexaenoic acid
Resolvin D6: RvD6; 4S,17S-dihydroxy-5Z,7Z,10Z,13Z,15E,19Z-docosahexaenoic acid
AT-Resolvin D1: AT-RvD1; 7S,8R,17R-trihydroxy-4Z,9E,11E,13Z,15E,19Z-docosahexaenoic acid
AT-Resolvin D2: AT-RvD2; 7S,16R,17R-trihydroxy-4Z,8E,10Z,12E,14E,19Z-docosahexaenoic acid
AT-Resolvin D3: AT-RvD3; 4D,11,17R-trihydroxy-5E,7E,9E,13Z,15E,19Z-docosahexaenoic acid
AT-Resolvin D4: AT-RvD4; 4S,5,17R-trihydroxy-6E,8E,10E,13E,15Z,19Z-docosahexaenoic acid
10S,17S-HDPAn-6: 10S,17S-dihydroxy-4Z,7Z,11E,13Z,15E-docosapentaenoic acid
7,17-HDPAn-6: 7,17-dihydroxy-4Z,8E,10Z,13Z,15E-docosapentaenoic acid
7,14-HDPAn-6: 7,14-dihydroxy-4Z,8E,10Z,12Z,16Z-docosapentaenoic acid
10S,17S-HDPAn-6: 10S,17S-dihydroxy-7Z,11E,13Z,15E,19Z-docosapentaenoic acid
7,17-HDPAn-6: 7,17-dihydroxy-8E,10Z,13Z,15E,19Z-docosapentaenoic acid
15S-HETE: 15S-hydroxy-5Z,8Z,11Z,13E-eicosatetraenoic acid
15R-HETE: 15R-hydroxy-5Z,8Z,11Z,13E-eicosatetraenoic acid
5S-HEPE: 5S-hydroxy-6E,8Z,11Z,14Z,17Z-eicosapentaenoic acid
5R-HEPE: 15R-hydroxy-5Z,8Z,11Z,13E,17Z-eicosapentaenoic acid
11S-HEPE: 11S-hydroxy-5Z,8Z,12E,14Z,17Z-eicosapentaenoic acid
11R-HEPE: 11R-hydroxy-5Z,8Z,12E,14Z,17Z-eicosapentaenoic acid
12S-HEPE: 12S-hydroxy-5Z,8Z,10E,14Z,17Z-eicosapentaenoic acid 12R-HEPE: 12R-hydroxy-5Z,8Z,10E,14Z,17Z-eicosapentaenoicacid
15S-HEPE: 15S-hydroxy-5Z,8Z,11Z,13E,17Z-eicosapentaenoic acid
15R-HEPE: 15R-hydroxy-5Z,8Z,11Z,13E,17Z-eicosapentaenoic acid
18S-HEPE: 18S-hydroxy-5Z,8Z,11Z,14Z,16E-eicosapentaenoic acid
18R-HEPE: 18R-hydroxy-5Z,8Z,11Z,14Z,16E-eicosapentaenoic acid
4S-HDHA: 4S-hydroxy-5E,7Z,10Z,13Z,16Z,19Z-docosahexaenoic acid
7S-HDHA: 7S-hydroxy-4Z,8E,10Z,13Z,16Z,19Z-docosahexaenoic acid
10S-HDHA: 10S-hydroxy-4Z,7Z,11E,13Z,16Z,19Z-docosahexaenoic acid
11S-HDHA: 11S-hydroxy-4Z,7Z,9E,13Z,16Z,19Z-docosahexaenoic acid
14S-HDHA: 14S-hydroxy-4Z,7Z,10Z,12E,16Z,19Z-docosahexaenoic acid
14R-HDHA: 14R-hydroxy-4Z,7Z,10Z,12E,16Z,19Z-docosahexaenoic acid
17S-HDHA: 17S-hydroxy-4Z,7Z,10Z,13Z,15E,19Z-docosahexaenoic acid
17R-HDHA: 17R-hydroxy-4Z,7Z,10Z,13Z,15E,19Z-docosahexaenoic acid
20S-HDHA: 20S-hydroxy-4Z,7Z,10Z,13Z,16Z,19Z-docosahexaenoic acid
17S-HDPAn-6: 17S-hydroxy-4Z,7Z,10Z,13Z,15E-docosapentaenoic acid
14S-HDPAn-6: 14S-hydroxy-4Z,7Z,10Z,12E,16Z-docosapentaenoic acid
10S-HDPAn-6: 10S-hydroxy-4Z,7Z,11E,13Z,16Z-docosapentaenoic acid
17S-HDPAn-3: 17S-hydroxy-7Z,10Z,13Z,15E,19Z-docosapentaenoic acid
14S-HDPAn-3: 17S-hydroxy-7Z,10Z,12E,16Z,19Z-docosapentaenoic acid
10S-HDPAn-6: 10S-hydroxy-7Z,11E,13Z,16Z,19Z-docosapentaenoic acid
17-HpDPAn-3: 17-hydroperoxy-8Z,10Z,13Z,15E,19Z-docosapentaenoic acid
RvD1n-3DPA: 7,8,17-trihydroxy-9,11,13,15E,19Z-docosapentaenoic acid
RvD2n-3DPA: 7,16,17-trihydroxy-8,10,12,14E,19Z-docosapentaenoic acid
RvD5n-3DPA: 7,17-trihydroxy-8E,10,13,15E,19Z-docosapentaenoic acid
PD1n-3DPA: 10,17-dihydroxy-7Z,11,13,15,19Z-docosapentaenoic acid
PD2n-3DPA: 16,17-dihydroxy-7Z,10,13,14,19Z-docosapentaenoic acid
14-HpDHA: 14-hydroperoxy-7Z,10Z,12E,16Z,19Z-docosapentaenoic acid
MaR1n-3DPA: 7,14-dihydroxy-8,10,12,16Z,19Z-docosapentaenoic acid
MaR2n-3DPA: 13,14-dihydroxy-7Z,9,11,16Z,19Z-docosapentaenoic acid
MaR3n-3DPA: 14,21-dihydroxy-7Z,10Z,12E,16Z,19Z-docosapentaenoic acid Compositions of the present disclosure comprise Omega-3 (e.g., EPA and/or DHA), 17-HDHA and 18-HEPE. In some embodiments, 17-HDHA and 18-HEPE are present in a total amount of about 0.0005% to about 1% by weight in the composition.

In some embodiments, the 17-HDHA is present in an amount of about 0.0002 wt. % to about 1 wt. %, for example about 0.0002 wt. %, 0.0004 wt. %, 0.0006 wt. %, 0.0008 wt. %, 0.001 wt. %, 0.002 wt. %, 0.003 wt. %, 0.004 wt. %, 0.005 wt. %, 0.006 wt. %, 0.007 wt. %, 0.008 wt. %, 0.009 wt. %, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.12 wt. %, 0.14 wt. %, 0.16 wt. %, 0.18 wt. %, 0.2 wt. %, about 0.22 wt. %, about 0.24 wt. %, about 0.26 wt. %, about 0.28 wt. %, about 0.3 wt. %, about 0.32 wt. %, about 0.34 wt. %, about 0.36 wt. %, about 0.38 wt. %, about 0.4 wt. %, about 0.42 wt. %, about 0.44 wt. %, about 0.46 wt. %, about 0.48 wt. %, about 0.5 wt. %, about 0.52 wt. %, about 0.54 wt. %, about 0.56 wt. %, about 0.58 wt. %, about 0.6 wt. %, about 0.62 wt. %, about 0.64 wt. %, about 0.66 wt. %, about 0.68 wt. %, about 0.7 wt. %, about 0.72 wt. %, about 0.74 wt. %, about 0.76 wt. %, about 0.78 wt. %, about 0.8 wt. %, about 0.82 wt. %, about 0.84 wt. %, about 0.86 wt. %, about 0.88 wt. %, about 0.9 wt. %, about 0.92 wt. %, about 0.94 wt. %, about 0.96 wt. %, about 0.98 wt. %, or about 1 wt. %.

In some embodiments, the 18-HEPE is present in an amount of about for example about 0.0002 wt. %, 0.0004 wt. %, 0.0006 wt. %, 0.0008 wt. %, 0.001 wt. %, 0.002 wt. %, 0.003 wt. %, 0.004 wt. %, 0.005 wt. %, 0.006 wt. %, 0.007 wt. %, 0.008 wt. %, 0.009 wt. %, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.12 wt. %, 0.14 wt. %, 0.16 wt. %, 0.18 wt. %, 0.2 wt. %, about 0.22 wt. %, about 0.24 wt. %, about 0.26 wt. %, about 0.28 wt. %, about 0.3 wt. %, about 0.32 wt. %, about 0.34 wt. %, about 0.36 wt. %, about 0.38 wt. %, about 0.4 wt. %, about 0.42 wt. %, about 0.44 wt. %, about 0.46 wt. %, about 0.48 wt. %, about 0.5 wt. %, about 0.52 wt. %, about 0.54 wt. %, about 0.56 wt. %, about 0.58 wt. %, about 0.6 wt. %, about 0.62 wt. %, about 0.64 wt. %, about 0.66 wt. %, about 0.68 wt. %, about 0.7 wt. %, about 0.72 wt. %, about 0.74 wt. %, about 0.76 wt. %, about 0.78 wt. %, about 0.8 wt. %, about 0.82 wt. %, about 0.84 wt. %, about 0.86 wt. %, about 0.88 wt. %, about 0.9 wt. %, about 0.92 wt. %, about 0.94 wt. %, about 0.96 wt. %, about 0.98 wt. %, or about 1 wt. %.

In some embodiments, the composition further comprises DPA. In some embodiments, the DPA is present in an amount of about 1 wt. % to about 10 wt. %, for example about 1 wt. %, about 2 wt. %, about 3 wt. %, about 4 wt. %, about 5 wt. %, about 6 wt. %, about 7 wt. %, about 8 wt. %, about 9 wt. %, or about 10 wt. %.

In some embodiments, the composition further comprises 14-HDHA. In some embodiments, the 14-HDHA is present in an amount of about 0.001 wt. % to about 0.1 wt. %, for example about 0.001 wt. %, about 0.002 wt. %, about 0.003 wt. %, about 0.004 wt. %, about 0.005 wt. %, about 0.006 wt. %, about 0.007 wt. %, about 0.008 wt. %, about 0.009 wt. %, about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, or about 0.1 wt. %.

In some embodiments, the composition further comprises 15-HETE. In some embodiments, the 15-HETE is present in an amount of about 0.0001 wt. % to about 0.01 wt. %, for example about 0.0001 wt. %, about 0.0002 wt. %, about 0.0003 wt. %, about 0.0004 wt. %, about 0.0005 wt. %, about 0.0006 wt. %, about 0.0007 wt. %, about 0.0008 wt. %, about 0.0009 wt. %, about 0.001 wt. %, about 0.0015 wt. %, about 0.002 wt. %, about 0.0025 wt. %, about 0.003 wt. %, about 0.0035 wt. %, about 0.004 wt. %, about 0.0045 wt. %, about 0.005 wt. %, about 0.0055 wt. %, about 0.006 wt. %, about 0.0065 wt. %, about 0.007 wt. %, about 0.0075 wt.

%, about 0.008 wt. %, about 0.0085 wt. %, about 0.009 wt. %, about 0.0095 wt. %, or about 0.01 wt. %.

In some embodiments, the composition further comprises 5-HETE. In some embodiments, the 5-HETE is present in an amount of about 0.0001 wt. % to about 0.01 wt. %, for example about 0.0001 wt. %, about 0.0002 wt. %, about 0.0003 wt. %, about 0.0004 wt. %, about 0.0005 wt. %, about 0.0006 wt. %, about 0.0007 wt. %, about 0.0008 wt. %, about 0.0009 wt. %, about 0.001 wt. %, about 0.0015 wt. %, about 0.002 wt. %, about 0.0025 wt. %, about 0.003 wt. %, about 0.0035 wt. %, about 0.004 wt. %, about 0.0045 wt. %, about 0.005 wt. %, about 0.0055 wt. %, about 0.006 wt. %, about 0.0065 wt. %, about 0.007 wt. %, about 0.0075 wt. %, about 0.008 wt. %, about 0.0085 wt. %, about 0.009 wt. %, about 0.0095 wt. %, or about 0.01 wt. %.

In some embodiments, the composition further comprises MaR-1. In some embodiments, the MaR-1 is present in an amount of about 0.0001 wt. % to about 0.01 wt. %, for example about 0.0001 wt. %, about 0.0002 wt. %, about 0.0003 wt. %, about 0.0004 wt. %, about 0.0005 wt. %, about 0.0006 wt. %, about 0.0007 wt. %, about 0.0008 wt. %, about 0.0009 wt. %, about 0.001 wt. %, about 0.0015 wt. %, about 0.002 wt. %, about 0.0025 wt. %, about 0.003 wt. %, about 0.0035 wt. %, about 0.004 wt. %, about 0.0045 wt. %, about 0.005 wt. %, about 0.0055 wt. %, about 0.006 wt. %, about 0.0065 wt. %, about 0.007 wt. %, about 0.0075 wt. %, about 0.008 wt. %, about 0.0085 wt. %, about 0.009 wt. %, about 0.0095 wt. %, or about 0.01 wt. %.

In some embodiments, the composition comprises pro-inflammatory compounds in a combined (e.g., total) amount of not more than about 0.005 wt. %, for example no more than about 0.005 wt. %, about 0.004 wt. %, about 0.003 wt. %, about 0.002 wt. %, about 0.001 wt. %, about 0.0005 wt. %, or no more than about 0.0001 wt. %.

In some embodiments, the composition comprises 12-HETE, LTB4, Prostaglandin E2, Prostaglandin D2, Thromboxane B2, Prostaglandin $F_{2\alpha}$, 20-COOH TLB4, 20-Hydoxy-LTB4, 11-HETE, 6-keto $PGF_{1\alpha}$, and 15-keto PGE2 in a combined (e.g., total) amount of not more than about 0.005 wt. %, for example no more than about 0.005 wt. %, about 0.004 wt. %, about 0.003 wt. %, about 0.002 wt. %, about 0.001 wt. %, about 0.0005 wt. %, or no more than about 0.0001 wt. %.

In some embodiments, the composition comprises a total amount of SPMs and SPM Precursors of about 0.01 wt. % to about 1 wt. %, for example about 0.01 wt. %, about 0.015 wt. %, about 0.02 wt. %, about 0.025 wt. %, about 0.03 wt. %, about 0.035 wt. %, about 0.04 wt. %, about 0.045 wt. %, about 0.05 wt. %, about 0.055 wt. %, about 0.06 wt. %, about 0.065 wt. %, about 0.07 wt. %, about 0.075 wt. %, about 0.08 wt. %, about 0.085 wt. %, about 0.09 wt. %, about 0.095 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, or about 1 wt. %

In some embodiments, the composition comprises Omega-3 fatty acids or derivatives thereof (e.g., an ester such as an ethyl ester) in a total amount of about 20 wt. % to about 99 wt. %, for example about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, about 85 wt. %, about 86 wt. %, about 87 wt. %, about 88 wt. %, about 89 wt. %, about 90 wt. %, about 91 wt. %, about 92 wt. %, about 93 wt. %, about 94 wt. %, about 95 wt. %, about 96 wt. %, about 97 wt. %, about 98 wt. %, about 99 wt. %, or greater than about 99 wt. %.

The Omega-3 fatty acids of the composition in a preferred embodiment are EPA and/or DHA, and in a more preferred embodiment, DHA is present in an amount of about 30% to about 45% and EPA is present in an amount of about 10% to about 26% by weight and 17-HDHA is present in an amount of about 0.0004% to about 0.04%, and 18-HEPE is present in an amount of about 0.0003% to about 0.04% by weight of the composition.

Omega-3 fatty acids, 17-HDHA and 18-HEPE can be obtained from different sources including vegetables, microbial, animal or combinations of these sources, including different oils as, for example, fish oil, krill oil, vegetable oil, microbial oil or combinations among other. In one embodiment, the Omega-3, 17-HDHA and 18-HEPE are obtained from fish oil, Krill oil and/or algae oil.

The chemical form of the Omega-3, 17-HDHA and 18-HEPE is selected from free fatty acids, esters, phospholipids, mono-glycerides, di-glycerides, tri-glycerides and combinations thereof. In one embodiment, the Omega-3 compounds are in ethyl ester form.

The composition is useful for a pharmaceutical composition, a dietary supplement, a nutraceutical product, a medical food composition, a nutritional composition for infant formulae and/or prenatal formulae that increases tissue levels of SPM in vivo.

In one embodiment, the composition is present in a capsule or other suitable dosage unit.

The composition can be obtained using a method selected from chromatography, extraction, distillation and/or vacuum rectification from several sources as, for example, fish oil and krill oil.

In one embodiment, the distillation is a short path molecular distillation process.

In several embodiments, the composition can be obtained from a crude oil using a process comprising several steps. The first step is a chemically esterification of the crude oil with ethanol and a basic catalyst at a temperature of about 55° C. to about 85° C. to produce an esterified oil.

This esterified oil is distilled to separate fatty acids shorter than 20 carbon atoms. This distillation is under vacuum of about 0.01 mbar to about 0.6 mbar and temperature of about 130° C. to about 190° C. for about 10 seconds to about 5 minutes to obtain a polyunsaturated fatty acid composition comprising about 20% to about 95% by weight EPA and/or DHA, and about 0.0005% to about 1% 17-HDHA and 18-HEPE by weight. This process can be covered in several stages in series.

In one embodiment, if necessary, after elimination of fatty acids shorter than 20 carbon atoms, the esterified oil can be distilled to eliminate fatty acids higher than 23 carbon atoms.

Before the step of distillation, to improve the quality of the composition and to remove oxidation, decomposition and/or degradation products, the polyunsaturated fatty acid composition is subjected to a supercritical fluid extraction (SFE) with $CO_2$ as supercritical fluid, pressure of about 80 bar to about 115 bar, and temperature of about 39° C. to about 46° C.

The oxidation, degradation and/or decomposition products eliminated by SFE can be selected from oligomers, dimers, polymers and conjugated dienes among others.

In various embodiments, the polyunsaturated composition is subjected to a step of bleaching under vacuum with bleaching earths and diatomaceous earths.

In an embodiment, the polyunsaturated oil composition is subjected to a transesterification step to obtain a composition containing a mixture of tri-glycerides and partial glycerides (mono-glycerides and di-glycerides). In one embodiment, the transesterification reaction can be catalyzed by lipases.

In various embodiments, polyunsaturated oil composition is subjected to a deodorization step under vacuum and a countercurrent flow of nitrogen or water steam.

In one embodiment, the composition is obtained from a starting material consisting of esterified concentrated oil, in these embodiments it is not necessary to make an esterification step.

The concentrated esterified oil is distilled to separate fatty acids shorter than 20 carbon atoms. This distillation is under vacuum of about 0.01 mbar to about 0.6 mbar and temperature of about 130° C. to about 190° C. for about 10 seconds to about 5 minutes to obtain a polyunsaturated fatty acid composition comprising about 20% to about 95% by weight EPA and/or DHA, and about 0.0005% to about 1% 17-HDHA and 18-HEPE by weight. This process can be covered in several stages in series.

In one embodiment, if necessary, after elimination of fatty acids shorter than 20 carbon atoms, the esterified oil can be distilled to eliminate fatty acids higher than 23 carbon atoms.

Before the step of distillation, to improve the quality of the composition and to remove oxidation, decomposition and/or degradation products, the polyunsaturated fatty acid composition is subjected to a supercritical fluid extraction (SFE) with $CO_2$ as supercritical fluid, pressure of about 80 bar to about 115 bar, and temperature of about 39° C. to about 46° C.

In one embodiment, the oxidation, degradation and/or decomposition products eliminated by SFE can be selected from oligomers, dimers, polymers and conjugated dienes, among others.

In one embodiment, the polyunsaturated oil composition, if necessary, can be subjected to a step of bleaching under vacuum with bleaching earths and diatomaceous earths.

In one embodiment, the polyunsaturated oil composition, if necessary, can be subjected to a transesterification to obtain a composition containing a mixture of tri-glycerides and partial glycerides (mono-glycerides and di-glycerides). In one embodiment, the transesterification can be made by lipases, such as lipase from *Candida antarctica*.

In one embodiment, if necessary, the polyunsaturated oil composition can be subjected to a deodorization step under vacuum and a countercurrent flow of nitrogen or water steam.

In various embodiments, the composition is useful in a method to increase phagocytic activity, comprising administering to a subject a phagocytic activity enhancing amount of the composition. In a preferred embodiment, the composition is useful in a method to enhance macrophage polarization toward an M2-like phenotype in a subject, comprising administering to the subject a macrophage polarization enhancing amount of the composition.

In one embodiment, the composition is useful for resolving inflammation associated with a disease in a subject, administering to the subject an inflammation-resolving amount of the composition.

The diseases can be selected from Crohn's disease, irritable bowel disease (IBD), fatty liver, wound healing, arterial inflammation, sickle-cell disease, arthritis, psoriasis, urticaria, vasculitis, asthma, ocular inflammation, pulmonary inflammation, dermatitis, cardiovascular diseases, AIDS, Alzheimer's disease, atherosclerosis, cancer, type 2 diabetes, hypertension, infectious diseases, leukemia/lymphoma, metabolic syndrome, neonatology, neuromuscular disorders, obesity, perinatal disorders, rheumatic diseases, stroke, surgical transplantation, vascular disorders, periodontal diseases, and brain injury.

In other embodiments, the composition can be used as a vaccine coadjuvant and/or as a chemotherapeutic coadjuvant.

In various embodiments, the composition comprises EPA in an amount between about 10% to about 26% by weight and DHA in an amount of about 30% to about 45% by weight, and 17-HDHA and 18-HEPE in a collective amount of about 0.0005% to about 1% by weight of the composition.

In one embodiment, the composition comprises EPA in an amount between about 10% to about 26% by weight and DHA in an amount of about 30% to about 45% by weight, 17-HDHA in an amount of about 0.0004% to about 0.04% by weight of the composition, and 18-HEPE in an amount of about 0.0003% to about 0.04% by weight of the composition.

The composition can further comprise DPA. In one embodiment, the composition comprises EPA and/or DHA and DPA in an amount between about 20% to about 95%, and 17-HDHA and 18-HEPE in an amount of about 0.0005% to about 1% by weight of the composition.

In some embodiments, the composition comprises EPA, DHA and DPA in an amount between about 20% to about 95%, and 17-HDHA and 18-HEPE in a collective amount of about 0.0005% to about 1% by weight of the composition.

In various embodiments, the composition also contains at least one additional SPM, such as 18R/S-HEPE, 17R/S-HDHA, 5S-HEPE, 15R/S-HEPE, 4R/S-HDHA, 7R/S-HDHA, 10R/S-HDHA, 14R/S-HDHA, and/or RvE1.

The Omega-3 fatty acid content in the composition is determined on a weight/weight percent basis relative to all fatty acids present in the composition as determined by methods such as those disclosed in the European Pharmacopeia monograph for Omega-3 fatty acids, European Pharmacopeia monograph method 2.49.29 or any equivalent method using gas chromatography, HPLC, FPLC, or other chromatographic method, and such content is expressed as a percentage in FFA content.

17-HDHA and 18-HEPE content of the composition is determined on a weight/weight basis relative to all fatty acids present in the composition using liquid chromatography-tandem mass spectrometry employing diagnostic transitions and co-elution with synthesized deuterated standards of 17-HDHA and 18-HEPE.

In some embodiments, the composition further comprises an acceptable carrier or excipient that may be administered by a variety of routes, for example, oral, topical, transdermal, parenteral, intravenous, intramuscular, rectal, sublingual, epidural, intracerebral, intraocular, subcutaneous, vaginal, transmucosal, intrathecal or intraarticular, among other acceptable carriers or excipients known to those of skill in the art.

The composition might also include one or more active ingredients, such as aspirin, curcumin, polyphenols, lutein, astaxanthin, and several vitamins (including vitamin C and vitamin E), among others.

In some embodiments, the composition can contain an antioxidant to improve stability of the composition.

In some embodiments, 17-HDHA and 18-HEPE can act as antioxidants in the composition.

The composition can be delivered in a variety of forms, such as capsules, pills, tablets, a powder, sachets, emulsions, suspensions, solutions, sprays for intranasal administration, aerosols, gels, soft and hard gelatin capsules, liposomes, chewable tablets, microsphere delivery systems, creams, sterile injectable solutions, an osmotic delivery system, dry powder inhalers, orally disintegrating tablets, oral sprays, hydrogels, dermal patches, transdermal patches, lotions, or syrups, among other delivery forms known in the art.

In some embodiments, the composition can be present in a capsule or other suitable dosage unit to be taken orally by a subject.

In some embodiments, the composition can be present in a soft or hard gelatin capsule with different sizes, shapes, colors and forms to address bioavailability enhancement, composition stability and other composition challenges.

In some embodiments, the composition can be delivered in an emulsion suitable for oral and/or parenteral administration to a subject. Such an emulsion can simplify the daily intake to just one sachet or spoon serving in oral administration and can also ensure minimal oxidation and good bioavailability of EPA, DHA, 17-HDHA and 18-HEPE in the composition, as well as increase the shelf life of the composition. Furthermore, parenteral nutrition can improve nutrient delivery to critically ill subjects.

EPA, DHA and DPA are commonly found in marine oils, including fish, algae and krill oil, among other oils, in contrast, ALA is commonly found in seeds, such as flax seeds, camelina seeds, and chia seeds, among others. These are not the exclusive sources of Omega-3, however: it can also be obtained from sources as vegetable, microbial, and animal, or combinations thereof.

In some embodiments, the Omega-3 fatty acids are obtained from an animal, vegetable and/or microbial source, alongside combinations of Omega-3 fatty acids obtained from different sources.

In some embodiments, the Omega-3 fatty acids are obtained from fish oil, krill oil, vegetable oil, microbial oil and/or combinations thereof.

In one embodiment, Omega-3 fatty acids are obtained from fish oil.

In one embodiment, Omega-3 fatty acids are obtained from krill oil.

In one embodiment, Omega-3 fatty acids are obtained from algae.

As described in WO 2013/170006, which is incorporated herein by reference in its entirety, SPMs, including 17-HDHA and 18-HEPE, can be found in different natural sources as fish, krill, algae or other organisms containing Omega-3 fatty acids.

In some embodiments, 17-HDHA and 18-HEPE are obtained from animal, vegetable and microbial sources.

In some embodiments, 17-HDHA and 18-HEPE are obtained from fish oil, krill oil, vegetable oil, microbial oil and combinations thereof.

In one embodiment, the 17-HDHA and 18-HEPE are obtained from fish oil.

In one embodiment, the 17-HDHA and 18-HEPE are obtained from krill oil.

In one embodiment, the 17-HDHA and 18-HEPE are obtained from algae.

Omega-3 fatty acids, 17-HDHA and 18-HEPE can be present in the composition in different chemical forms, including free fatty acids, esters, phospholipids, monoglycerides, di-glycerides, tri-glycerides, and combinations thereof.

In an embodiment, Omega-3 fatty acids are in ethyl ester form in the composition.

In an embodiment, the 17-HDHA and 18-HEPE are in ethyl ester form in an amount of at least 80% by weight, and in a mixture of partial glycerides (tri-glycerides, monoglycerides and di-glycerides).

In one embodiment, EPA, DHA, 17-HDHA and 18-HEPE are in ethyl ester form.

The composition can be obtained using a variety of methods, for example, chromatography, extraction, supercritical extraction, distillation and vacuum rectification, and/or any other method generally known to those skilled in the art of isolating and purifying Omega-3 polyunsaturated fatty acids.

The composition can be obtained from two different starting materials consisting in a crude oil or an esterified concentrated oil.

In various embodiments, the crude oil or the esterified concentrated oil is obtained from marine oil, vegetable oil, microbial oil, and mixtures of these oils.

In various embodiments, the crude oil or the esterified concentrated marine oil is fish oil and/or krill oil.

In one embodiment, the crude oil or the esterified concentrated oil is obtained from fish oil.

In one embodiment, the oils can be obtained from anchovy, sardine, Jack mackerel, mackerel, tuna, salmon, Pollock, krill and/or algae.

In one embodiment, the crude oil or the esterified concentrated oil is obtained from krill oil.

In one embodiment, the crude oil or the esterified concentrated oil is obtained from algae oil.

In various embodiments, when a crude oil is used as a starting material, the first step is a chemical esterification of the oil with ethanol and a basic catalyst, at a temperature of about 55° C. to about 85° C., to produce an esterified oil.

In an embodiment, the basic catalyst used in the chemical esterification is sodium ethoxide (EtONa).

In an embodiment, the basic catalyst used in the chemical esterification is potassium hydroxide (KOH).

This esterified oil is distilled to separate fatty acids shorter than 20 carbon atoms. This distillation is under vacuum of about 0.01 mbar to about 0.6 mbar and temperature of about 130° C. to about 190° C. for about 10 seconds to about 5 minutes to obtain a polyunsaturated fatty acid composition comprising about 20% to about 95% by weight EPA and/or DHA, and about 0.0005% to about 1% 17-HDHA and 18-HEPE by weight.

In one embodiment, if necessary, after elimination of fatty acids shorter than 20 carbon atoms, the esterified oil can be distilled to eliminate fatty acids higher than 23 carbon atoms.

In one embodiment, the distillation is a short path molecular distillation process.

These distillation steps to eliminate fatty acids shorter than 20 carbon atoms can be covered in several stages in series, until a polyunsaturated fatty acid composition comprising the desired composition is obtained.

Before the step of distillation, to improve the quality of the composition and to remove oxidation, decomposition and/or degradation products, the polyunsaturated fatty acid composition is subjected to a supercritical fluid extraction (SFE) with $CO_2$ as supercritical fluid, pressure of about 80 bar to about 115 bar, and temperature of about 39° C. to about 46° C.

In an embodiment, the oxidation, decomposition and/or degradation products eliminated by SFE comprise one or more of oligomers, dimers, polymers and conjugated dienes.

In an embodiment, the process, if necessary, can further comprise a step of bleaching the polyunsaturated fatty acid composition under vacuum with bleaching earths and diatomaceous earths.

In an embodiment, the process further comprises a step of transesterification of the polyunsaturated fatty acid composition to obtain a composition containing a mixture of tri-glycerides and partial glycerides (mono-glycerides and di-glycerides).

This transesterification yields a composition comprising a mixture of tri-glycerides and partial glycerides (mono-glycerides and di-glycerides).

In an embodiment, this transesterification is catalyzed by lipases.

In a preferred embodiment, lipases are active as of about 25° C., with an optimum temperature of about 50° C. to about 70° C.

In one embodiment, the reaction of transesterification is carried out under vacuum.

In an embodiment, the polyunsaturated oil composition, if necessary, can be subjected to a deodorization step under vacuum and a countercurrent flow of nitrogen or water steam.

In a preferred embodiment, the deodorization step under vacuum is performed at a temperature of about 130° C. to about 200° C.

When the starting material is esterified concentrated oil, the process is the same as that described above, but without the first step of esterification of the starting material.

In various embodiments, this concentrated oil is distilled to separate fatty acids shorter than 20 carbon atoms. This distillation is under vacuum of about 0.01 mbar to about 0.6 mbar and temperature of about 130° C. to about 190° C. for about 10 seconds to about 5 minutes to obtain a polyunsaturated fatty acid composition comprising about 20% to about 95% by weight EPA and/or DHA, and about 0.0005% to about 1% 17-HDHA and 18-HEPE by weight.

These distillation steps to eliminate fatty acids shorter than 20 carbon atoms can be covered in several stages in series, until a polyunsaturated fatty acid composition comprising the desired composition is obtained.

In one embodiment, if necessary, after elimination of fatty acids shorter than 20 carbon atoms, the concentrated oil can be distilled to eliminate fatty acids higher than 23 carbon atoms.

In one embodiment, the distillation is a short path molecular distillation process.

Before the step of distillation, to improve the quality of the composition and to remove oxidation, decomposition and/or degradation products, the polyunsaturated fatty acid composition is subjected to a supercritical fluid extraction (SFE) with $CO_2$ as supercritical fluid, pressure of about 80 bar to about 115 bar, and temperature of about 39° C. to about 46° C.

In an embodiment, the process, if necessary, can further comprise a step of bleaching the polyunsaturated fatty acid composition under vacuum with bleaching earths and diatomaceous earths.

In an embodiment, the process further comprises a step of transesterification of the polyunsaturated fatty acid composition to obtain a composition containing a mixture of tri-glycerides and partial glycerides (mono-glycerides and di-glycerides).

This transesterification yields a mixture of tri-glycerides and partial glycerides (mono-glycerides and di-glycerides).

In an embodiment, this transesterification is catalyzed by lipases.

In one embodiment, lipases are active as of about 25° C., with an optimum temperature of about 50° C. to about 70° C.

In one embodiment, the reaction of transesterification is carried out under vacuum.

In an embodiment, the polyunsaturated oil composition, if necessary, can be subjected to a deodorization step under vacuum and a countercurrent flow of nitrogen or water steam.

In a preferred embodiment, the deodorization step under vacuum is performed at a temperature of about 130° C. to about 200° C.

Phagocytosis is an important physiological process characterized by the ingestion of foreign particles and killing of microorganisms by phagocytic leukocytes (granulocytes, monocytes and macrophages). Phagocytosis involves a complex series of events including, for example, production of pro- and anti-inflammatory cytokines and chemokines. Deficiencies in phagocytosis cause several pathological conditions (i.e., chronic inflammatory diseases) and cause severe and recurrent microbial (bacterial and fungal) infections.

The activation of non-phlogistic (non-fever causing) phagocytosis and polarization of macrophages toward an M2-like phenotype is an essential step for the resolution of the inflammatory response and complete homeostasis of adipose tissue. Several SPMs, including RvD1, RvD2, Protectin D1, and Mar-1 (maresin 1), have been established as mediators that stimulate macrophage switching to the M2 phenotype.

In some embodiments, the composition is useful to increase phagocytic activity of macrophages in a subject, administering to the subject a phagocytic activity enhancing amount of a composition.

When comparing the activation of macrophages through this application with Omacor and a 3624 EE, the results show that Omacor and 3624 EE reduce the activation of macrophages; instead, the composition of interest produces an increase of phagocytic activity and polarization of macrophages toward a pro-resolution state (i.e., M2) (shown in example 2).

In one embodiment, the increase of the phagocytic activity of the composition is at least 55% of the maximum value obtained for Mar-1 at concentration 1 nM.

In some embodiments, the present disclosure provides methods for stimulating macrophage activation and polarization toward a pro-resolution state (i.e., M2) in a subject by enhancing the amount of SPMs and/or SPM Precursor species present in a naturally occurring oil composition.

In one embodiment, the polyunsaturated fatty acid composition features methods to elevate SPM levels in plasma in a subject by administering to the subject an effective amount of the composition effective to elevate SPM levels in a subject.

RvD1 has been established as an activator of non-phlogistic phagocytosis in macrophages, which is an essential step for the resolution of the inflammatory response.

In some embodiments, the composition features methods to elevate RvD1 levels in plasma in a subject by administering to the subject an effective amount of the composition to elevate RvD1 level in a subject.

Figure 3:
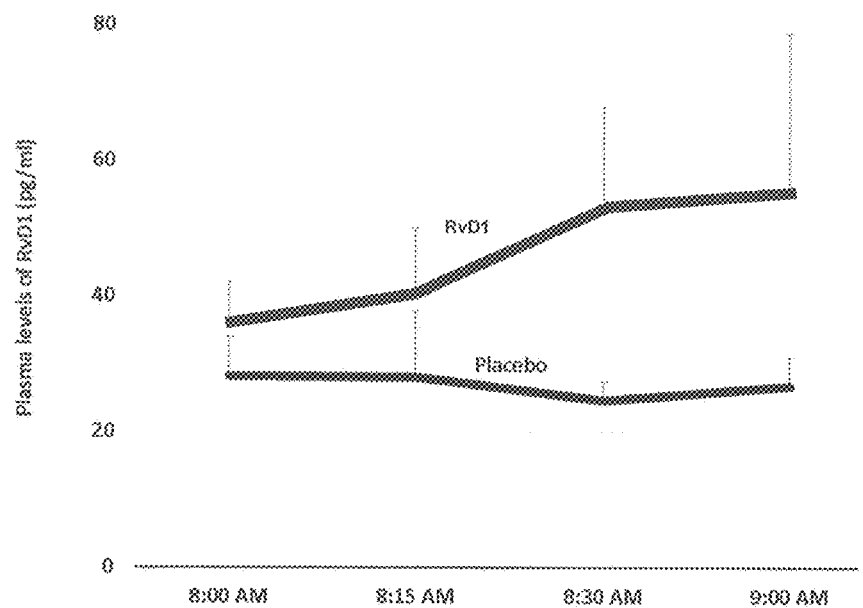
FIG. 3: Levels of RvD1 (pg/ml) measured in human plasma samples. This figure shows the values of RvD1 measured in plasma in subjects administered a composition containing EPA, DHA, 17-HDHA and 18-HEPE compared with a placebo.

In one embodiment, subjects who were administered 4 capsules of a composition containing 250 mg per capsule, as shown in FIG. 3, experienced a 53% greater elevation in plasma levels of RvD1 than subjects who were administered a placebo.

In one preferred embodiment, the plasma elevation is produced one hour after the administration of the capsules.

In one embodiment, the effective amount to elevate RvD1 in plasma levels in a subject is a daily dose of at least 300 mg DHA, approximately 100 mg EPA, ~12.5 µg of 17-HDHA, and ~10 µg of 18-HEPE.

In another preferred embodiment, the effective amount to elevate RvD1 in plasma levels in a subject is a daily dose of at least ~1200 mg DHA, ~400 mg EPA, ~50 µg of 17-HDHA and ~40 µg of 18-HEPE.

In some embodiments, the polyunsaturated fatty acid composition features methods for treating and resolving inflammation in a subject (e.g., a human being, dog, cat, horse and other animals) having a disease with an inflammatory component by administering to the subject an effective amount of the composition in an amount effective to activate resolution mechanisms and thus resolve local inflammation.

In several embodiments, the diseases with an inflammatory component can be selected from Crohn's disease, IBD, ulcerative colitis, fatty liver, wound healing, arterial inflammation, sickle-cell disease, arthritis, psoriasis, urticaria, vasculitis, asthma, ocular inflammation, pulmonary inflammation, dermatitis, cardiovascular diseases, AIDS, Alzheimer's disease, atherosclerosis, cancer, type 2 diabetes, hypertension, infectious diseases, leukemia/lymphoma, metabolic syndrome, neonatology, neuromuscular disorders, obesity, perinatal disorders, rheumatic diseases, stroke, surgical transplantation, vascular disorders, periodontal diseases, brain injury, trauma and neuronal inflammation, among others.

In some embodiments, the composition can be manufactured as a pharmaceutical composition, a dietary supplement, a nutraceutical product, a medical food composition, and a nutritional composition for infant formulae and/or prenatal formulae.

In other embodiments, the composition can be used as a vaccine coadjuvant to potentiate the immune response to an antigen and/or modulate it towards the desired immune response.

The tumour microenvironment, orchestrated largely by inflammatory cells, is an indispensable participant in the neoplastic process, fostering proliferation, survival and migration of the tumour cells. Now it is well known that inflammation is a critical component of tumour progression.

In another embodiment, due to the inflammatory component associated with cancer and the inflammation-resolving character of the composition, the composition can be useful as a chemotherapeutic coadjuvant.

In some embodiments, the present disclosure provides a polyunsaturated fatty acid composition comprising about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a dietary supplement, nutraceutical product, or medical food composition comprising a composition comprising about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a nutritional composition for infant formulae and/or prenatal formulae comprising a composition comprising about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a pharmaceutical composition comprising a composition comprising about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a process for obtaining a composition as disclosed herein from an oil using a method selected from chromatography, extraction, distillation and/or vacuum rectification. In some embodiments, the composition comprises about 20% to about 95%, by weight, Omega-3 fatty acids, and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a process for obtaining a composition as disclosed herein from a crude oil, the process comprising: (i) chemically esterifying crude oil with ethanol and a basic catalyst, at a temperature of about 55° C. to about 75° C. to produce esterified oil; (ii) distilling the esterified oil, under vacuum of about 0.01 mbar to about 0.6 mbar and at a temperature of about 130° C. to 190° C. for about 10 seconds to about 5 minutes to separate fatty acids shorter than 20 carbons to obtain a distilled esterified oil comprising about 20% to about 95% by weight EPA and/or DHA, and about 0.0005% to 1% by weight 17-HDHA and 18-HEPE; and (ii) subjecting the polyunsaturated fatty acid composition obtained in step (ii) to supercritical fluid extraction with $CO_2$ as a supercritical fluid at a temperature of about 39° C. to 46° C. and pressure of about 80 bar to 115 bar to remove oxidation, decomposition and/or degradation products as oligomers, dimers, polymers and conjugated dienes from the composition. In some embodiments, step (ii) is made in several stages in series. In some embodiments, the process further comprises distilling the esterified oil obtained in step (ii) to remove fatty acids containing more than 23 carbon atoms in the corresponding fatty acid chains before step (iii). In some embodiments, the process further comprises bleaching the polyunsaturated fatty acid composition under vacuum with bleaching earths and diatomaceous earths. In some embodiments, the process further comprises transesterifying the polyunsaturated fatty acid composition in ethyl ester form to obtain a composition containing a mixture of tri-glycerides, mono-glycerides and di-glycerides. In some embodiments, the transesterifying comprises catalysis with one or more lipases. In some embodiments, the process further comprises deodorizing the composition of interest by applying a counterflow of nitrogen or water steam to the composition under vacuum. In some embodiments, the oil is obtained from fish, krill, vegetable, and/or microbes. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a process for obtaining a polyunsaturated fatty acid composition from a concentrated esterified oil comprising: (i) distilling the concentrated esterified oil under vacuum of about 0.01 mbar to 0.6 mbar and at a temperature of about 130° C. to about 190° C. for about 10 seconds to about 5 minutes to separate fatty acids having fewer than 20 carbon atoms in the corresponding fatty acid chain to obtain a distilled esterified oil comprising about 20% to about 95% by weight EPA and/or DHA, and about 0.0005% to about 1% by weight 17-HDHA and 18-HEPE; (ii) subjecting the distilled esterified oil obtained in step (i) to supercritical fluid extraction with $CO_2$ as a supercritical fluid at a temperature of about 20° C. to 40° C. and at a pressure of about 80 bar to about 115 bar to remove oxidation, decomposition and degradation products as oligomers, dimers, polymers and conjugated dienes from the composition. In some embodiments, step (i) is made in several stages in series. In some embodiments, the process further comprises distilling the distilled esterified oil obtained in step (i) to remove fatty acids having more than 23 carbon atoms in the corresponding fatty acid chain before step (ii). In some embodiments, the process further comprises bleaching the polyunsaturated fatty acid ethyl ester composition under vacuum with bleaching earths and diatomaceous earths. In some embodiments, the process further comprises transesterifying the polyunsaturated fatty acid ethyl ester composition to obtain a composition containing a mixture of tri-glycerides, mono-glycerides and di-glycerides. In some embodiments, the transesterifying comprises catalysis with one or more lipases. In some embodiments, the process further comprises deodorizing the polyunsaturated fatty acid ethyl ester composition of interest by applying a counterflow of nitrogen or water steam to the composition under vacuum. In some embodiments, the concentrated esterified oil is obtained from fish, krill, vegetable, and/or microbes. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a method of increasing phagocytic activity of macrophages in a subject, comprising administering to the subject a phagocytic activity enhancing amount of a composition as disclosed herein. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a method of enhancing macrophage polarization toward a pro-resolution phenotype in a subject, comprising administering to the subject a macrophage polarization enhancing amount of a composition as disclosed herein. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a method of resolving inflammation associated with a disease in a subject in need thereof, comprising administering to the subject an inflammation-resolving amount of a composition as disclosed herein. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof. In some embodiments, the disease is selected from Crohn's disease, irritable bowel disease ("IBD"), fatty liver, wound healing, arterial inflammation, sickle-cell disease, arthritis, psoriasis, urticaria, vasculitis, asthma, ocular inflammation, pulmonary inflammation, dermatitis, cardiovascular diseases, AIDS, Alzheimer's disease, atherosclerosis, cancer, type 2 diabetes, hypertension, infectious diseases, leukemia/lymphoma, metabolic syndrome, neonatology, neuromuscular disorders, obesity, perinatal disorders, rheumatic diseases, stroke, surgical transplantation, vascular disorders, periodontal diseases, brain injury, trauma and neuronal inflammation.

In some embodiments, the present disclosure provides a method for elevating SPM levels in plasma of a human subject, comprising administering to the human subject a composition as disclosed herein. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof. In some embodiments, the SPM comprises RvD1.

In some embodiments, the present disclosure provides a use of a composition as disclosed herein as a vaccine coadjuvant. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a use of a composition as disclosed herein as a chemotherapeutic coadjuvant. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a composition as disclosed herein for increasing phagocytic activity of macrophages in a subject. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a composition as disclosed herein for enhancing macrophage polarization toward a pro-resolution phenotype in a subject. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a composition as disclosed herein for resolving inflammation associated with a disease in a subject in need thereof. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof. In some embodiments, the disease is selected from Crohn's disease, irritable bowel disease (IBD), fatty liver, ulcerative colitis, wound healing, arterial inflammation, sickle-cell disease, arthritis, psoriasis, urticaria, vasculitis, asthma, ocular inflammation, pulmonary inflammation, dermatitis, cardiovascular diseases, AIDS, Alzheimer's disease, atherosclerosis, cancer, type 2 diabetes, hypertension, infectious diseases, leukemia/lymphoma, metabolic syndrome, neonatology, neuromuscular disorders, obesity, perinatal disorders, rheumatic diseases, stroke, surgical transplantation, vascular disorders, periodontal diseases, brain injury, trauma and neuronal inflammation.

In some embodiments, the present disclosure provides a composition as disclosed herein for elevating SPM levels in plasma of a human subject. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof. In some embodiments, the SPM comprises RvD1.

In some embodiments, the present disclosure provides a use of a composition as disclosed herein in the manufacture of a medicament for increasing phagocytic activity of macrophages in a subject. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a use of a composition as disclosed herein in the manufacture of a medicament for enhancing macrophage polarization toward a pro-resolution phenotype in a subject. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof.

In some embodiments, the present disclosure provides a use of a composition as disclosed herein in the manufacture of a medicament for resolving inflammation associated with a disease in a subject in need thereof. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof. In some embodiments, the disease is selected from Crohn's disease, irritable bowel disease ("IBD"), fatty liver, ulcerative colitis, wound healing, arterial inflammation, sickle-cell disease, arthritis, psoriasis, urticaria, vasculitis, asthma, ocular inflammation, pulmonary inflammation, dermatitis, cardiovascular diseases, AIDS, Alzheimer's disease, atherosclerosis, cancer, type 2 diabetes, hypertension, infectious diseases, leukemia/lymphoma, metabolic syndrome, neonatology, neuromuscular disorders, obesity, perinatal disorders, rheumatic diseases, stroke, surgical transplantation, vascular disorders, periodontal diseases, brain injury, trauma and neuronal inflammation.

In some embodiments, the present disclosure provides a use of a composition as disclosed herein in the manufacture of a medicament for elevating SPM levels in plasma of a human subject. In some embodiments, the composition comprises about 20% to about 95%, by weight, Omega-3 fatty acids and 17-HDHA and 18-HEPE in a total amount of about 0.0005% to about 1%, by weight. In some embodiments, the composition further comprises an acceptable carrier. In some embodiments, the composition is present in a capsule or other suitable dosage unit. In some embodiments, the Omega-3 fatty acids comprise DHA and/or EPA. In some embodiments, the DHA is present in an amount of about 30% to about 45% by weight of the composition; the EPA is present in an amount of about 10% to about 26% by weight of the composition; the 17-HDHA is present in an amount of about 0.0004% to about 0.04% by weight of the composition; and the 18-HEPE is present in an amount of about 0.0003% to about 0.04% by weight of the composition. In some embodiments, the composition further comprises DPA. In some embodiments, the composition further comprises 14-HDHA, optionally 5-HETE, and optionally 7R,14S-dihydroxy-4Z,8E,10E,12Z,16Z,19Z-docosahexaenoic acid ("MaR1"). In some embodiments, the Omega-3 fatty acids, 17-HDHA and 18-HEPE are obtained from a vegetable, a microbe, an animal, or a combination thereof. In some embodiments, the Omega-3 fatty acids, 17-HDHA and 18-HEPE are obtained from fish oil, krill oil, vegetable oil, microbial oil, or a combination thereof. In some embodiments, the Omega-3 fatty acids, 17-HDHA and 18-HEPE are obtained from fish oil. In some embodiments, the Omega-3 fatty acids are in the form of free fatty acids, esters, phospholipids, mono-glycerides, di-glycerides, tri-glycerides and/or combinations thereof. In some embodiments, the Omega-3 fatty acids are in ethyl ester form. In some embodiments, the 17-HDHA and 18-HEPE are in the form of free fatty acids, esters, phospholipids, mono-glycerides, di-glycerides, tri-glycerides and/or combinations thereof. In some embodiments, the 17-HDHA and 18-HEPE are in the form of mono-glycerides, di-glycerides, tri-glycerides and/or combinations thereof. In some embodiments, the SPM comprises RvD1.

EXAMPLES

Example 1. Obtain an Oil Fraction Comprising DHA, EPA, 17-HDHA and 18-HEPE from Semi-Refined Marine Oil Six compositions of polyunsaturated fatty acids containing Omega-3 (20-95% by weight), 17-HDHA and 18-HEPE (about 0.0005-1% by weight) are included as examples of compositions of the present disclosure.

The determination of the Omega-3 content was performed using European Pharmacopeia 2.4.29 method and determination of 17-HDHA and 18-HEPE was performed by liquid chromatography-tandem mass spectrometry employing diagnostic transition and co-elution with synthesized deuterated standards of 17-HDHA and 18-HEPE.

1.1 LM03-1.

This composition was obtained from a starting material consisting on esterified concentrated marine oil.

Esterified semirefined marine oil was then injected in a continuous flow rate in a vacuum distillation unit, composed mainly for an evaporator, that works at high vacuum in this example at 0.08-0.12 mbar and high temperature (140-144° C.), and within the time of exposure of the material at these conditions from 10 seconds to 5 minutes. In this stage an ethyl ester rich in fatty acids mainly shorter than C20 is distilled off. Then, the obtained marine oil was distilled to remove the higher components (with more than 23 carbon atoms), working at 0.09-0.12 mbar in pressure and 140-157° C. in temperature.

These steps have been covered in two times in series.

To improve the quality of the composition and remove oxidation, decomposition and degradation products as oligomers, dimers, polymers and conjugated dienes, the composition was subjected to a supercritical fluid extraction (SFE) by counter current extraction on a column with carbon dioxide at supercritical conditions, working at 44.5-45.5° C. in temperature and at a pressure of 80-86 bar.

The composition obtained contained a total amount of Omega-3 of about 629.9 mg/g (as FFA), DHA in an amount of about 342.1 mg/g (as FFA), EPA in an amount of about 187.6 mg/g (as FFA), 17-HDHA in an amount of about 60.8 mg/kg and 18-HEPE in an amount of about 87.5 mg/kg with 1.4 mg/g of a mixed natural tocopherols to improve the oxidative stability of the product. The analytical data and content of this fraction is shown in Table 1.

TABLE 1

| Analysis of LM03-1 | | |
|---|---|---|
| Determination | Result | Method |
| SPM content | | |
| 17HDHA (mg/kg) | 60.8 | LC/MS |
| 18HEPE (mg/kg) | 87.5 | LC/MS |
| 17HDHA + 18HEPE (mg/kg) | 148.3 | LC/MS |
| Fatty acid profile | | |
| EPA (mg/g as FFA) | 187.6 | Eur. Ph. 2.4.29 |
| DHA (mg/g as FFA) | 342.1 | Eur. Ph. 2.4.29 |
| Total Omega-3 (mg/g as FFA) Sum of 18:3 ω-3, 18:4 ω-3, 20:4 ω-3, 20:5 ω-3, 21:5 ω-3, 22:5 ω-3, 22:6 ω-3 | 629.9 | Eur. Ph. 2.4.29 |

The analysis of the chemical status of 17-HDHA and 18-HEPE in fraction LM03.1 is shown in Table 2, where the percentages of each chemical form are expressed by weight.

TABLE 2

Distribution of chemical forms of SPMs in LM03-1

| | |
|---|---|
| % 17-HDHA (EE)in LM03-1 | 88.67 |
| % 17-HDHA in other chemical form (mono-glyceride, Di-glyceride, tri-glyceride and FFA) in LM03-1 | 11.33 |
| % 18-HEPE (EE)in LM03-1 | 87.52 |
| % 18-HEPE in other chemical form (mono-glyceride, Di-glyceride, tri-glyceride and FFA) in LM03-1 | 12.48 |

1.2 LM03-2.

This composition was obtained from a starting material consisting on esterified concentrated marine oil.

Esterified semirefined marine oil was then injected in a continuous flow rate in a vacuum distillation unit, composed mainly for an evaporator, that works at high vacuum in this example at 0.08-0.12 mbar and high temperature (140-144° C.), and within the time of exposure of the material at these conditions from 10 seconds to 5 minutes. In this stage an ethyl ester rich in fatty acids mainly shorter than C20 was distilled off. Then, the obtained marine oil was redistilled to reduce once more time the shorter fatty acids working at 0.09-0.12 mbar in pressure and 140-157° C. in temperature. This final fraction and the obtained as distillate in the first stage were mixed and then distilled, in two stages in series: in the first stage working at 0.08-0.12 mbar of pressure and 140-144° C. of temperature and, in the second stage, working at 0.09-0.12 mbar in pressure and 140-157° C. in temperature.

To improve the quality of the composition and remove oxidation, decomposition and degradation products as oligomers, dimers, polymers and conjugated dienes, the composition was subjected to a supercritical fluid extraction (SFE) by counter current extraction on a column with carbon dioxide at supercritical conditions, working at 44.5-45.5° C. in temperature and at a pressure of 80-86 bar.

LM03-2 contained a total amount of Omega-3 of about 600 mg/g (as FFA), DHA in an amount of about 300.0 mg/g (as FFA), EPA in an amount of about 100.0 mg/g (as FFA), 17-HDHA in an amount of about 50.0 mg/kg and 18-HEPE in an amount of about 40.0 mg/kg with a maximum of 1.4 mg/g of a mixed natural tocopherols to improve the oxidative stability of the product. The analytical data and content of this fraction is shown in Table 3.

TABLE 3

Analysis of LM03-2

| Determination | Result | Method |
|---|---|---|
| SPM content | | |
| 17HDHA (mg/kg) | 50.0 | LC/MS |
| 18HEPE (mg/kg) | 40.0 | LC/MS |
| 17HDHA + 18HEPE (mg/kg) | 90.0 | LC/MS |
| Fatty acid profile | | |
| EPA (mg/g as FFA) | 100.0 | Eur. Ph. 2.4.29 |
| DHA (mg/g as FFA) | 300.0 | Eur. Ph. 2.4.29 |
| Total Omega-3 (mg/g as FFA) | 600.0 | Eur. Ph. 2.4.29 |
| Sum of 18:3 ω-3, 18:4 ω-3, 20:4 ω-3, 20:5 ω-3, 21:5 ω-3, 22:5 ω-3, 22:6 ω-3 | | |

1.3. LM03-3.

This composition was obtained using the process described above from a starting material consisting on esterified concentrated marine oil.

Esterified semirefined marine oil was then injected in a continuous flow rate in a vacuum distillation unit, composed mainly for an evaporator, that works at high vacuum in this example at 0.08-0.12 mbar and high temperature (150-154° C.), and within the time of exposure of the material at these conditions from 10 seconds to 5 minutes. In this stage an ethyl ester rich in fatty acids mainly shorter than twenty carbons was distilled off. Then, the obtained marine oil was redistilled to reduce once more time the shorter fatty acids working at 0.08-0.12 mbar in pressure and 155-165° C. in temperature.

To improve the quality of the composition and remove oxidation, decomposition and degradation products as oligomers, dimers, polymers and conjugated dienes, the composition was subjected to a supercritical fluid extraction (SFE) by counter current extraction on a column with carbon dioxide at supercritical conditions, working at 44.5-45.5° C. in temperature and at a pressure of 80-86 bar.

The composition LM03-3 obtained contained a total amount of Omega-3 of about 663.0 mg/g (as FFA), including DHA in an amount of about 441.7 mg/g (as FFA), and EPA in an amount of about 112.7 mg/g (as FFA). LM03-3 also contained significant amounts of 17-HDHA, 18-HEPE, 14-HDHA, 5-HETE and maresin 1 (MaR1), and no significant amounts of pro-inflammatory in an amount of about 65.2 mg/kg with a maximum of 1.1 mg/g of a mixed natural tocopherols to improve the oxidative stability of the product. The analytical data and content of this fraction is shown in Table 4.

TABLE 4

Analysis of LM03-3

| | Component | Abundance | wt. % |
|---|---|---|---|
| SPMs/SPM Precursors | 18-HEPE | 278550 µg/kg | 0.02786 wt. % |
| | 17-HDHA | 146748 µg/kg | 0.01467 wt. % |
| | 14-HDHA | 97715 µg/kg | 0.00977 wt. % |
| | maresin 1 | 7545 µg/kg | 0.00075 wt. % |
| | 15-HETE | 6970 µg/kg | 0.00070 wt. % |
| | 5-HETE | 5474 µg/kg | 0.00055 wt. % |
| | RvE3 | 2617 µg/kg | 0.00026 wt. % |
| | RvD5 | 1241 µg/kg | 0.00012 wt. % |
| | MaR1 n-3DPA | 827 µg/kg | 0.00008 wt. % |
| | RvD6 | 440 µg/kg | 0.00004 wt. % |
| | PD1 | 397 µg/kg | 0.00004 wt. % |
| | RvD5m-3DPA | 332 µg/kg | 0.00003 wt. % |
| | RvD2n-3DPA | 186 µg/kg | 0.00002 wt. % |
| | RvE2 | 179 µg/kg | 0.00002 wt. % |
| | RvD1 | 173 µg/kg | 0.00002 wt. % |
| | RvE1 | 112 µg/kg | 0.00001 wt. % |
| | lipoxin B4 | 126 µg/kg | 0.00001 wt. % |
| | RvD4 | 97 µg/kg | 0.00001 wt. % |
| | lipoxin A4 | 94 µg/kg | 0.00001 wt. % |
| | RvD2 | 83 µg/kg | 0.00001 wt. % |
| | RvD1n-3DPA | 7 µg/kg | 0.00000 wt. % |
| | RvD3 | 5 µg/kg | 0.00000 wt. % |
| | TOTAL SPM/SPM PRECURSORS: | 549917 µg/kg | 0.05499 wt. % |
| Pro-Inflamma-tories | 12-HETE | 2878 µg/kg | 0.00029 wt. % |
| | LTB4 | 669 µg/kg | 0.00007 wt. % |
| | Prostaglandin E2 | 564 µg/kg | 0.00006 wt. % |
| | Prostaglandin D2 | 300 µg/kg | 0.00003 wt. % |
| | Thromboxane B2 | 56 µg/kg | 0.00001 wt. % |
| | Prostaglandin $F_{2\alpha}$ | 34 µg/kg | 0.00000 wt. % |
| | TOTAL PRO-INFLAMMATORIES: | 4501 µg/kg | 0.00045 wt. % |
| ω-3 Fatty Acids | DHA (as free fatty acid) | 441.7 mg/g | 44.17 wt. % |
| | EPA (as free fatty acid) | 112.7 mg/g | 11.27 wt. % |

TABLE 4-continued

Analysis of LM03-3

| Component | Abundance | wt. % |
|---|---|---|
| Other Omega-3 Fatty Acids* | 108.6 mg/g | 10.86 wt. % |
| TOTAL OMEGA-3 FATTY ACIDS | 663.0 mg/g | 66.30 wt. % |

*18:3ω-3, 18:4 ω-3, 20:4 ω-3, 21:5 ω-3, and 22:5 ω-3.

1.4. LM03-4.

This composition was obtained from a starting material consisting on semirefined marine oil.

Esterified semirefined marine oil was then injected in a continuous flow rate in a vacuum distillation unit, composed mainly for an evaporator, working at high vacuum (0.18 to 0.20 mbar) and high temperature (140° C. to 150° C.), and within the time of exposure of the material at these conditions from 10 seconds to 5 minutes. In this stage an ethyl ester rich in fatty acids mainly shorter than twenty carbons was distilled off. Then, the obtained marine oil was distilled to remove the higher components (with more than 23 carbon atoms), working at 155-172° C. and 0.18 to 0.20 mbar.

The obtained fraction was distilled in a second stage, working in the first stage 0.08-0.12 mbar of pressure and 140-144° C. of temperature and, in the second stage, working at 0.09-0.12 mbar in pressure and 140-157° C. in temperature.

Intermediate product was then processed in a urea complexation step to reduce the content of saturated and monounsaturated fatty acids. Urea was solved in ethanol and intermediate product is added. When, urea was precipitated from this solution, by forming adduct products with mainly saturated and monounsaturated ethyl esters. The urea adduct was removed by filtration, and ethanol was recovered by distillation. The resulting ethyl esters were washed with demineralized water. This step can be done in two stages in series.

A bleaching step was performed then, to control and reduce urea traces.

The composition obtained contained a total amount of Omega-3 of about 870.0 mg/g (as FFA), DHA in an amount of about 345.0 mg/g (as FFA), EPA in an amount of about 425.0 mg/g (as FFA), 17-HDHA in an amount of about 56.2 mg/kg and 18 HEPE in an amount of about 96.4 mg/kg with a maximum of 4.8 mg/g of a-tocopherol to improve the oxidative stability of the product. The analytical data and content of this fraction is shown in Table 5.

TABLE 5

Analysis of LM03-4

| Determination | Result | Method |
|---|---|---|
| SPM content | | |
| 17HDHA (mg/kg) | 56.2 | LC/MS |
| 18HEPE (mg/kg) | 96.4 | LC/MS |
| 17HDHA + 18HEPE (mg/kg) | 152.6 | LC/MS |
| Fatty acid profile | | |
| EPA (mg/g as FFA) | 425.0 | Eur. Ph. 2.4.29 |
| DHA (mg/g as FFA) | 345.0 | Eur. Ph. 2.4.29 |

TABLE 5-continued

Analysis of LM03-4

| Determination | Result | Method |
|---|---|---|
| Total Omega-3 (mg/g as FFA) Sum of 18:3 ω-3, 18:4 ω-3, 20:4 ω-3, 20:5 ω-3, 21:5 ω-3, 22:5 ω-3, 22:6 ω-3 | 870.0 | Eur. Ph. 2.4.29 |

1.5. LM03-5

This composition was obtained from a starting material consisting on semirefined marine oil.

Semirefined marine oil was esterified to form ethyl esters, by contacting with ethanol and a basic catalyst (EtONa), at 55-65° C. a known quantity of ethanol and catalyst are added to the reactor. After the reaction time (2-4 hours) concluded, the excess of additives were evaporated. Then, a final washing step was included in order to neutralize the semirefined marine oil esterified.

The composition obtained LM03-5 contained a total amount of Omega-3 of about 316.0 mg/g (as FFA), DHA in an amount of about 104.0 mg/g (as FFA), EPA in an amount of about 152.0 mg/g (as FFA), n-3 DPA in an amount of about 19.0 mg/g (as FFA) 17-HDHA in an amount of about 14.6 mg/kg and 18-HEPE in an amount of about 35.8 mg/kg. The analytical data and content of this fraction is shown in Table 6.

TABLE 6

Analysis of LM03-5

| Determination | Result | Method |
|---|---|---|
| SPM content | | |
| 17HDHA (mg/kg) | 14.6 | LC/MS |
| 18HEPE (mg/kg) | 35.8 | LC/MS |
| 17HDHA + 18HEPE (mg/kg) | 50.4 | LC/MS |
| Fatty acid profile | | |
| EPA (mg/g as FFA) | 152.0 | Eur. Ph. 2.4.29 |
| DHA (mg/g as FFA) | 104.0 | Eur. Ph. 2.4.29 |
| DPA (mg/g as FFA) | 19.0 | Eur. Ph. 2.4.29 |
| Total Omega-3 (mg/g as FFA) Sum of 18:3 ω-3, 18:4 ω-3, 20:4 ω-3, 20:5 ω-3, 21:5 ω-3, 22:5 ω-3, 22:6 ω-3 | 316.0 | Eur. Ph. 2.4.29 |

1.6. LM03-6

This composition was obtained from a starting material consisting on esterified concentrated marine oil.

Esterified semirefined marine oil was then injected in a continuous flow rate in a vacuum distillation unit, composed mainly for an evaporator, that works at high vacuum in this example at 0.08-0.12 mbar and high temperature (140-144° C.), and within the time of exposure of the material at these conditions from 10 seconds to 5 minutes. In this stage an ethyl ester rich in fatty acids mainly shorter than C20 was distilled off. Then, the obtained marine oil was distilled to remove the higher components (with more than 23 carbon atoms), working at 0.09-0.12 mbar in pressure and 140-157° C. in temperature. These steps have been covered in two times in series To improve the quality of the composition and remove oxidation, decomposition and degradation products as oligomers, dimers, polymers and conjugated dienes, the composition was subjected to a supercritical fluid extraction (SFE) by counter current extraction on a column with carbon dioxide at supercritical conditions, working at 44.5-45.5° C. in temperature and at a pressure of 80-86 bar.

The composition obtained was subjected to a step of transesterification to obtain a composition containing a mixture of tri-glycerides and partial glycerides (mono-glycerides and di-glycerides).

The reaction of transesterification was catalyzed by lipases at a temperature of about 50° C. to about 70° C. under vacuum.

The obtained fraction was treated under vacuum with high temperatures and a countercurrent flow of steam (nitrogen) to remove the volatile components and improve the odour, if they are present. These volatile components were solved into the steam and flow out the deodorization equipment.

The composition obtained LM03-6 contained a total amount of Omega-3 of about 635.0 mg/g (as FFA), DHA in an amount of about 189.0 mg/g (as FFA), EPA in an amount of about 342.0 mg/g (as FFA), 17-HDHA in an amount of about 126.8 mg/kg and 18-HEPE in an amount of about 95.2 mg/kg with a maximum of 4 mg/g of a mixed natural tocopherols to improve the oxidative stability of the product. The analytical data and content of this fraction is shown in Table 7.

TABLE 7

Analysis of LM03-6

| Determination | Result | Method |
|---|---|---|
| SPM content | | |
| 17HDHA (mg/kg) | 126.8 | LC/MS |
| 18HEPE (mg/kg) | 95.2 | LC/MS |
| 17HDHA + 18HEPE (mg/kg) | 222.0 | LC/MS |
| Fatty acid profile | | |
| EPA (mg/g as FFA) | 342.0 | Eur. Ph. 2.4.29 |
| DHA (mg/g as FFA) | 189.0 | Eur. Ph. 2.4.29 |
| Total Omega-3 (mg/g as FFA) Sum of 18:3 ω-3, 18:4 ω-3, 20:4 ω-3, 20:5 ω-3, 21:5 ω-3, 22:5 ω-3, 22:6 ω-3 | 635.0 | Eur. Ph. 2.4.29 |

Example 2. Study of Regulation of Phagocytosis In Vitro Employing the Spectrophotometric Evaluation of Phagocytized Zymosan Bioparticles in PMA-Stimulated THP-1 Cells Macrophages play a central role in inflammation and host defense against microorganisms, and also participate actively in the resolution of inflammation after alternative activation from pro-inflammatory macrophages switched towards anti-inflammation (M2-like phenotype).

To determine the capacity of promoting a macrophage pro-resolution phenotype (i.e. M2) and therefore to foster the resolution of inflammation, several oils were tested in a human macrophage model adapted by López Vicario C from a method previously described (Titos et al., 2011) and compared with Mar-1 (the term Maresins is coined from Macrophage mediator in resolving inflammation), an established active compound in resolution of the inflammation.

THP-1 cells were cultured in a 96-well black plate at a density of 3.5×10⁴ cells/well in 200 μl RPMI 1640 medium (10% FBS). Cells were differentiated into macrophages with 50 ng/ml of phorbol 12-myristate 13-acetate (PMA) for 2 days and then, maintained with fresh RPMI medium (10% FBS) for 1 day. Then the macrophages were washed by aspiration ×2 with sterile DPBS–/– and pretreated for 15 minutes with 150 μl of the compounds to be tested or vehicle (ethanol) using RPMI without phenol red (1% FBS). Each sample was tested in duplicate or triplicate.

The compounds tested in this macrophage model were:
Maresin 1 (from Cayman Chemicals)
LM03-1 (a total amount of Omega-3 of about 629.9 mg/g (as FFA), DHA in an amount of about 342.1 mg/g (as FFA), EPA in an amount of about 187.6 mg/g (as FFA), 17-HDHA in an amount of about 60.8 mg/kg and 18-HEPE in an amount of about 87.5 mg/kg with 1.4 mg/g of a mixed natural tocopherols—3624 EE (about 33.0% EPA ethyl ester and about 22% DHA in ethyl ester form expressed as FFA)
Omacor (about 42.5% EPA ethyl ester and about 34.5% DHA in ethyl ester form expressed as FFA)

The concentration of Mar-1 used in the experiment was 1 nM, which has been determined the concentration with maximum activity in phagocytic activation for this compound in previous experiments using this model (data not shown). The oils tested, LM03-1, 3624 EE and Omacor, were diluted 1/10³ for use in the experiment.

After 15 minutes of pretreatment with the compounds to be tested, 50 μl of opsonized zymosan bioparticles (Molecular Probes; Z-2841; ratio cell/bioparticles=1/10) were added to each well of the plate (Final volume=200 μl) and mixed.

The macrophages were incubated at 37° C. for 60 minutes and then the plate was centrifuged for 5 minutes at 400 g at room temperature and supernatant was discarded by aspiration.

The macrophages were washed with sterile DPBS–/– before adding 100 μl of Trypan Blue Solution (diluted at 1:10 in sterile DPBS–/–) to quench fluorescence of bioparticles bound to the outside of the cell.

Then, the macrophages were incubated for 2 minutes at room temperature and centrifuged for 5 minutes at 400 g at room temperature and the excess of Trypan Blue was aspirated.

The fluorescent intensity of each sample was read in the fluorescence microplate reader FLUOstar OPTIMA (in a Costar 96 microplate) and average fluorescence intensity values were calculated to obtain phagocytosis response to the effector.

Maresin-1, a very potent inducer of macrophage phagocytosis was used as a reference. 100% activity was assigned to compare the effect over phagocytic activity of the other compounds tested.

Figure 2:
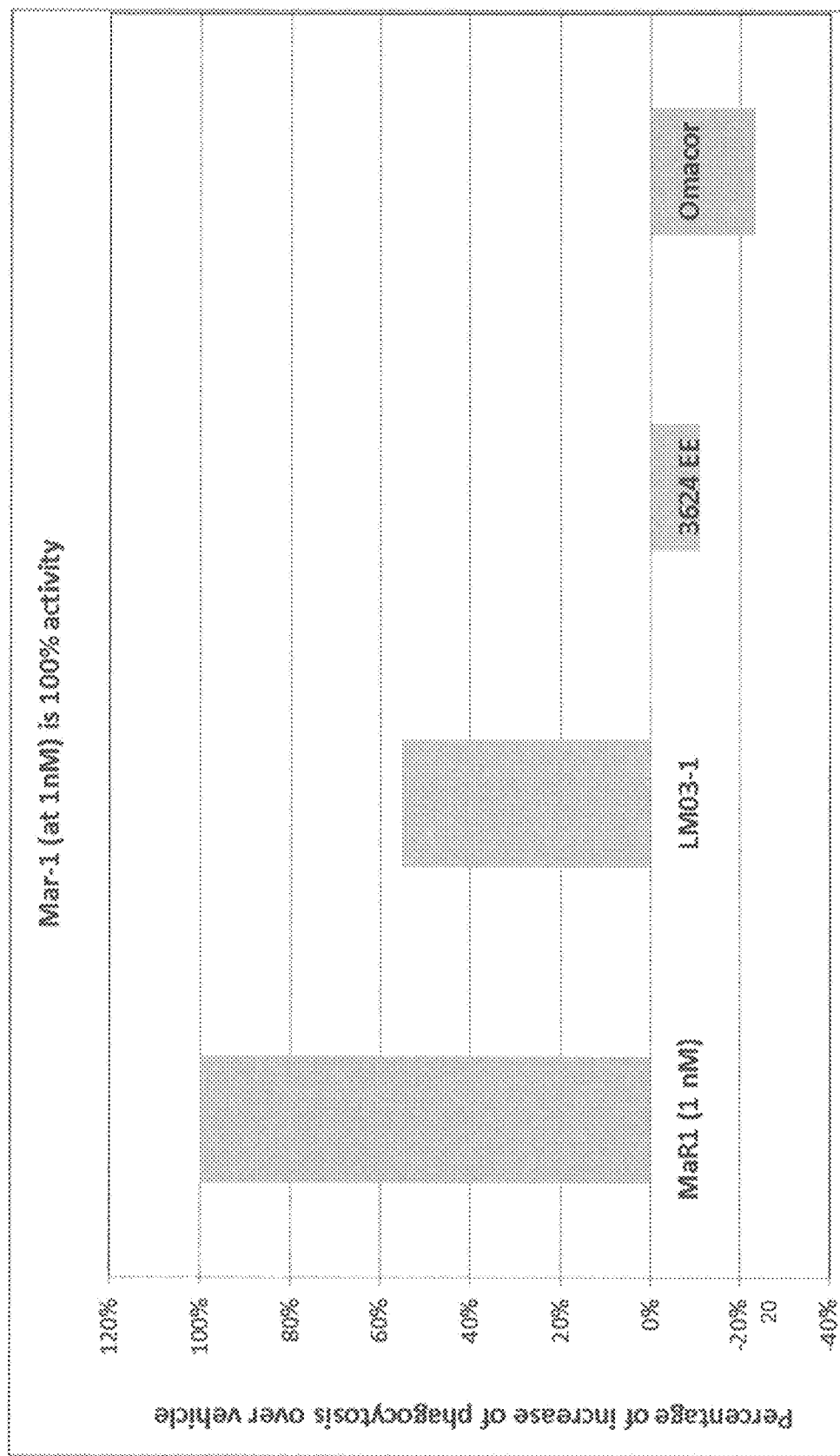
FIG. 2: Percentage of increase of phagocytosis over vehicle comparative. This figure shows the comparison of macrophage activation in an in vitro model of three oil fractions in ethyl ester form compared to the values obtained with Mar-1 (1 nM). In this model 100% activity is assigned to Mar-1 (1 nM) over phagocytic activity.

The LM03-1 oil, as shown in FIG. 2, activated macrophage activation reaching more than 55% of the activity of Mar-1 (pure compound) in macrophage activation. LM03-1 oil fraction enhanced macrophage activity and polarization toward a pro-resolution phenotype (I.E. M2) due to its SPMs. The results obtained in this model indicate the resolution capacity of LM03-1 oil fraction.

The other products tested in this model, 3624 EE and Omacor, did not activate phagocytosis activity much more, instead, these compounds diminished the phagocytic activity of macrophages in this model.

Example 3. Study of Plasma Levels of RvD1 During a 1 Hour Period after Ingesting a Composition Containing DHA, EPA, 17-HDHA, and 18-HEPE To determine the variation in plasma levels of RvD1 after ingest a ethyl ester Omega-3 oil fraction containing EPA, DHA, 17-HDHA and 18-HEPE (LM03-2 oil fraction obtained in Example 1) compared with a placebo, a clinical study was designed over N=10 subjects administered LM03-2 composition and compared with N=5 subjects ingesting a placebo.

The composition of LM03-2 used in this clinical trial contained a total amount of Omega-3 of about 600 mg/g (as FFA), DHA in an amount of about 300.0 mg/g (as FFA), EPA in an amount of about 100.0 mg/g (as FFA), 17-HDHA in an amount of about 50.0 mg/kg and 18-HEPE in an amount of about 40.0 mg/kg.

The subject characteristics of the study appear in Table 8.

TABLE 8

Subject characteristics of the study

| Variable | LM03-2 (n = 10) | Placebo (N = 5) | P-value |
|---|---|---|---|
| Age (y) | 46.0 ± 2.4 | 51.4 ± 4.5 | 0.259 |
| Height (m) | 1.66 ± 0.01 | 1.69 ± 0.03 | 0.379 |
| Weight (kg) | 90.0 ± 5.6 | 88.5 ± 6.3 | 0.870 |
| BMI | 32.6 ± 1.9 | 31.2 ± 2.2 | 0.657 |
| CRP (mg/l) | 5.25 ± 1.2 | 5.84 ± 1.3 | 0.772 |

Subjects ingested 4 capsules (250 mg each capsule) of LM03-2 or placebo at 8:00 am, blood samples were collected before ingestion of the capsules and 15 min, 30 min and one hour post-ingestion.

LM03-2 composition of each capsule is approximately 75 mg DHA, 25 mg EPA, and SPM precursors 17-HDHA (17.5 µg) and 18-HEPE (10 µg).

RvD1 has been identified as an activator of non-phlogistic phagocytosis in macrophages, which is an essential step for the resolution of the inflammatory response. The blood samples were analyzed for plasma RvD1 levels and results are shown in FIG. 3. The increase of RvD1 levels in subjects one hour after the ingestion of 4 capsules of LM03-2 composition is 53% higher than the level just after the ingestion of the composition in these subjects, instead the levels of RvD1 one hour later in subjects that ingested a placebo raised a 5% over their initial value.

This results show the capacity of the composition LM03-2 to elevate RvD1 levels in plasma.

Example 4. Mice Subcutaneous Anti-Inflammatory Activity Trial

To determine the anti-inflammatory activity of different oils, three oils were tested for their anti-inflammatory activity and compared with the activity of indomethacin (a nonsteroidal anti-inflammatory drug) in a subcutaneous in vivo model of inflammation using CD1 white male mice, adult (30-35 grams weight).

N=5 mice were used in each group tested with an oil fraction group and N=4 mice were used in control and indomethacin groups.

A prototypical inflammatory agent, LPS (lipopolysaccharide from the outer coat of bacteria) was injected subcutaneously as a single dose (5 mg per kg in a 200 µL volume) in the dorsal hind flank to create inflammation in mice.

Thirty minutes prior to the administration of LPS, 100 µL of vehicle control (PBS phosphate buffer saline), indomethacin, or one of the oil fractions were administered by gavage.

Neutrophil infiltration into the site of inflammation was measured non-invasively by bioluminescence emitted by conversion of luminol by the neutrophil enzyme myeloperoxidase. 150 µL of a suspension of luminol in PBS (50 mg/l) was administered to the mice and the image was taken after 15 minutes of the luminol injection.

The bioluminescence was measured using an IVIS-lumina equipment (Perkin-Elmer, Tres Cantos, Madrid, Spain).

The method used generates reproducible bioluminescence measurements of neutrophil activity in order to be able to measure statistically significant changes in neutrophil activity upon administration of different oil fractions and indomethacin.

The oils fractions tested in the experiments are as follows:
Krill: Tri-glyceride and phospholipids form (about 14.4% EPA and 7.4% DHA in weight expressed as FFA).
LM03-3 containing a total amount of Omega-3 of about 663.0 mg/g (as FFA), DHA in an amount of about 441.7 mg/g (as FFA), EPA in an amount of about 112.7 mg/g (as FFA), and about 550 mg/kg of total SPMs/SPM Precursors, including 17-HDHA in an amount of about 146 mg/kg and 18-HEPE in an amount of about 279 mg/kg.
Algae: Tri-glyceride form (about 0.2% EPA and 39.7% DHA in weight expressed as FFA).

The results for the analysis of bioluminescence for each oil fraction compared with control and indomethacin are shown in two figures per compound tested, measure the total flux of the bioluminescence radiation (net radiance photons/sec) and the evolution of medium radiance (photons/sec/cm$^2$/sr) along time.

Figure 4A:
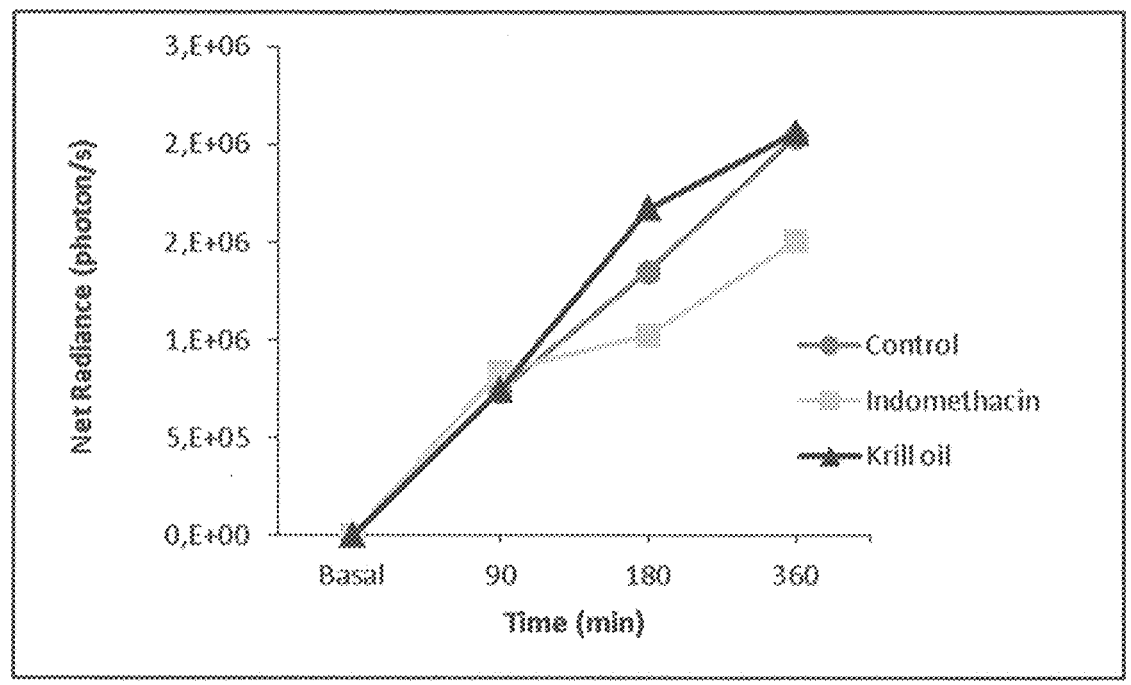
FIGS. 4A and 4B: Total and average flux values. These figures show an analysis of bioluminescence total flux of the bioluminescence value (bottomless) and the evolution of medium signal value (bottomless) in an inflammatory murine model administered by gavage krill oil and compared with indomethacin and control.
Figure 4B:
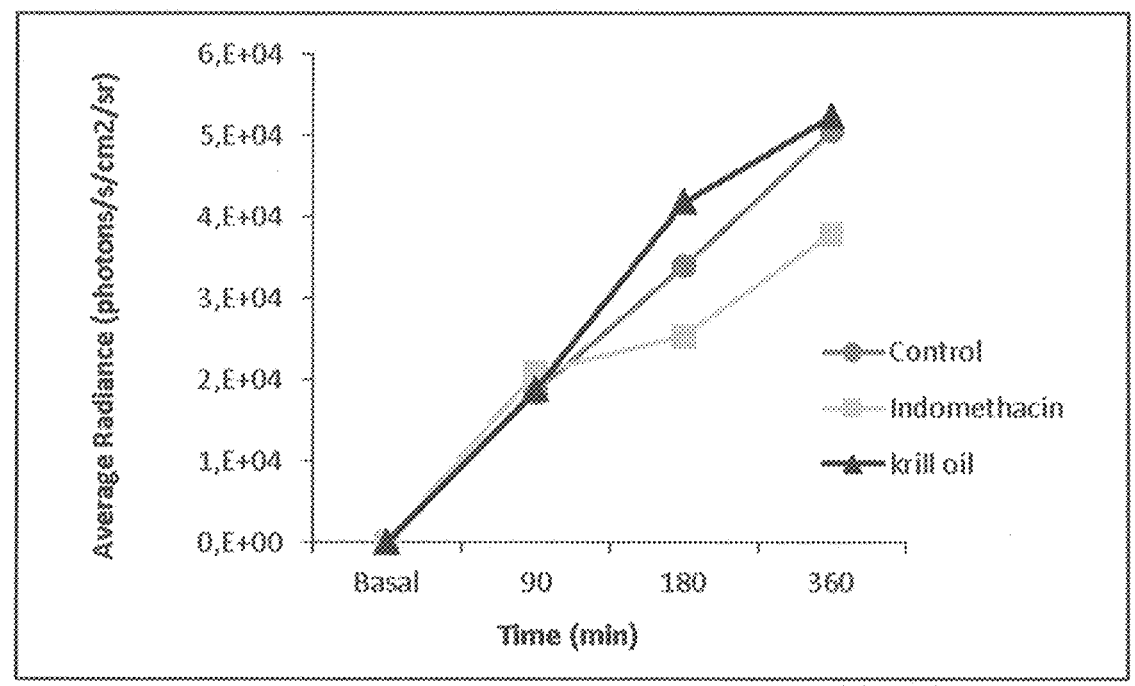

For krill oil, the response shown in FIGS. 4A and 4B was similar to the control and even over the control at 180 minutes. The response compared with the indomethacin was 37% higher, showing a significant value of p<0.02. As shown in FIGS. 4A and 4B, krill oil was not significantly anti-inflammatory in this model.

Figure 5A:
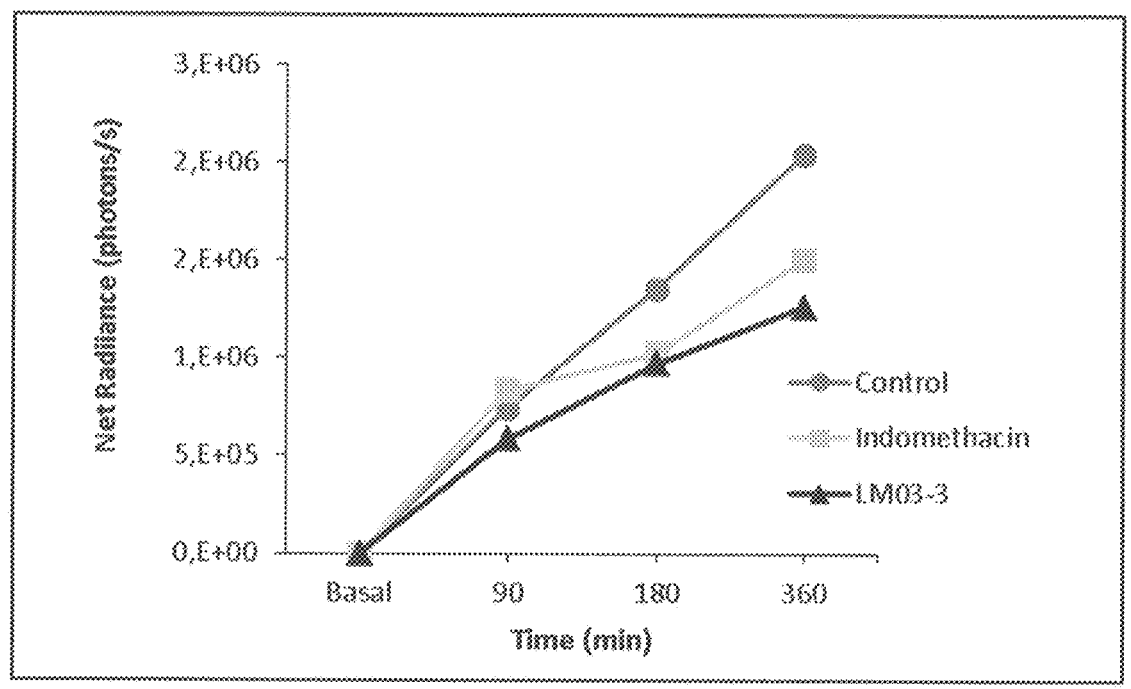
FIGS. 5A and 5B: Total and average flux values. These figures show an analysis of bioluminescence total flux of the bioluminescence value (bottomless) and the evolution of medium signal value (bottomless) in an inflammatory murine model administered by gavage LM03-3 oil and compared with indomethacin and control.
Figure 5B:
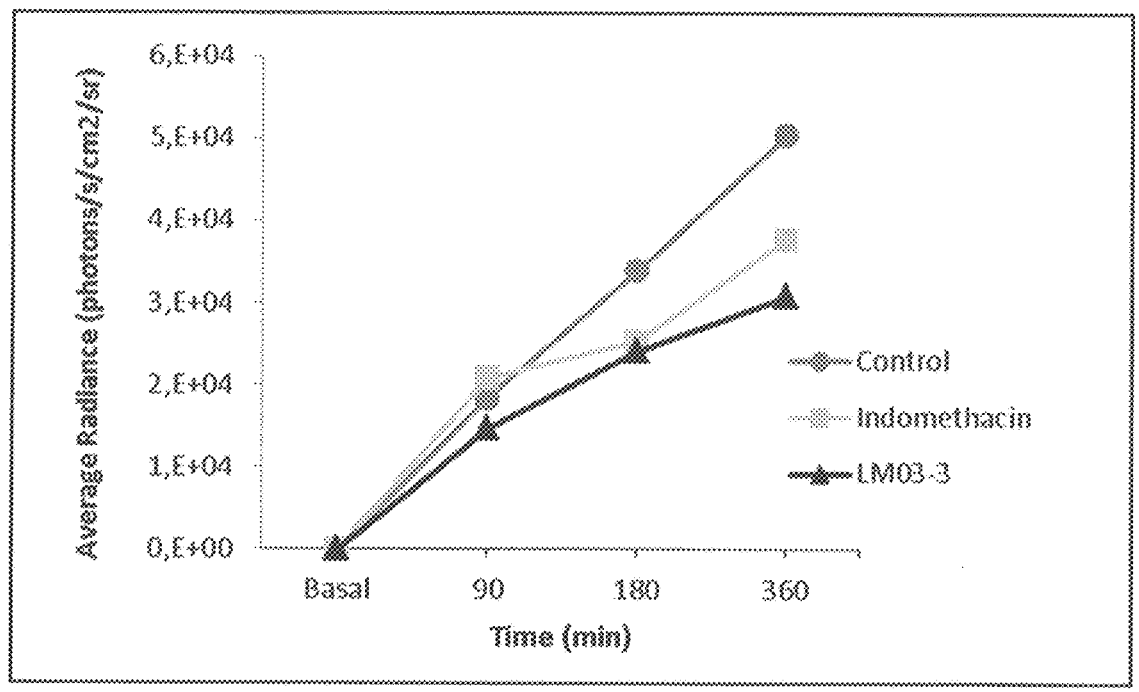

The results detailed in FIGS. 5A and 5B, probe the anti-inflammatory character of fraction LM03-3. LM03-3 oil shows a clear anti-inflammatory effect at 90, 180 and 360 minutes with a quick response at 90 min and the effect is maintained during the 6 hours that last the experiment. This is the only tested oil that shows this quick and long effect.

At time 180 minutes, the LM03-3 oil had the maximum difference compared to the control, with the total flux (photons/sec) 36% below the control (p<0.13).

Figure 6A:
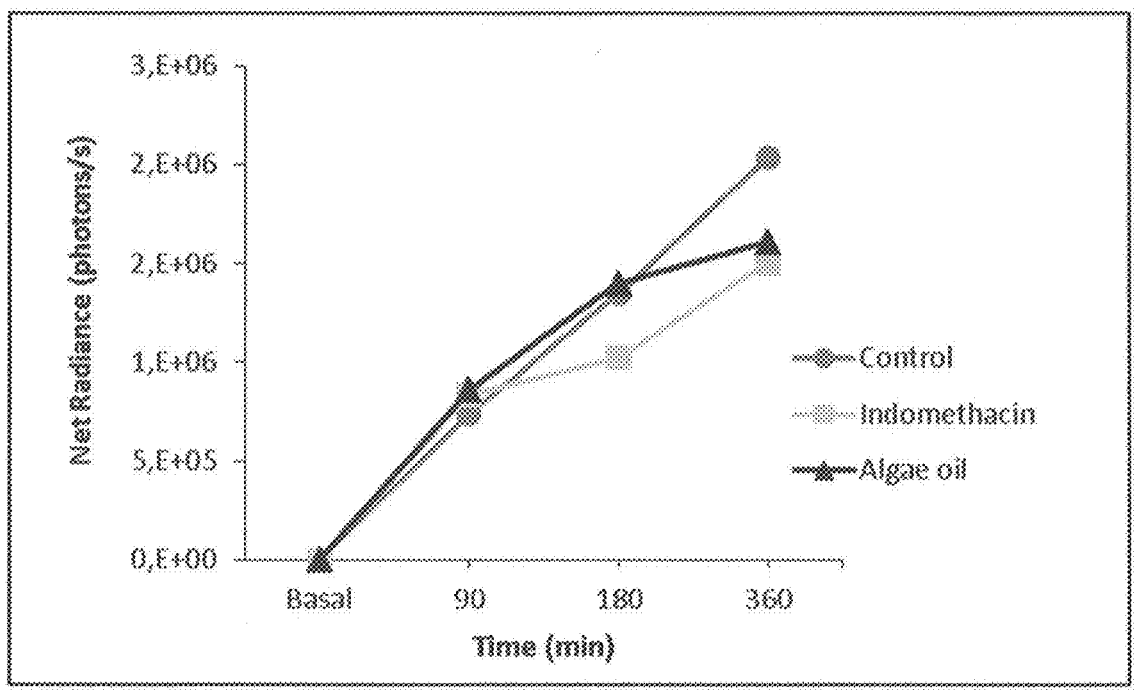
FIGS. 6A and 6B: Total and average flux values. These figures show an analysis of bioluminescence total flux of the bioluminescence radiation value (bottomless) and the evolution of medium radiance value (bottomless) in an inflammatory murine model administered by gavage algae oil and compared with indomethacin and control.
Figure 6B:
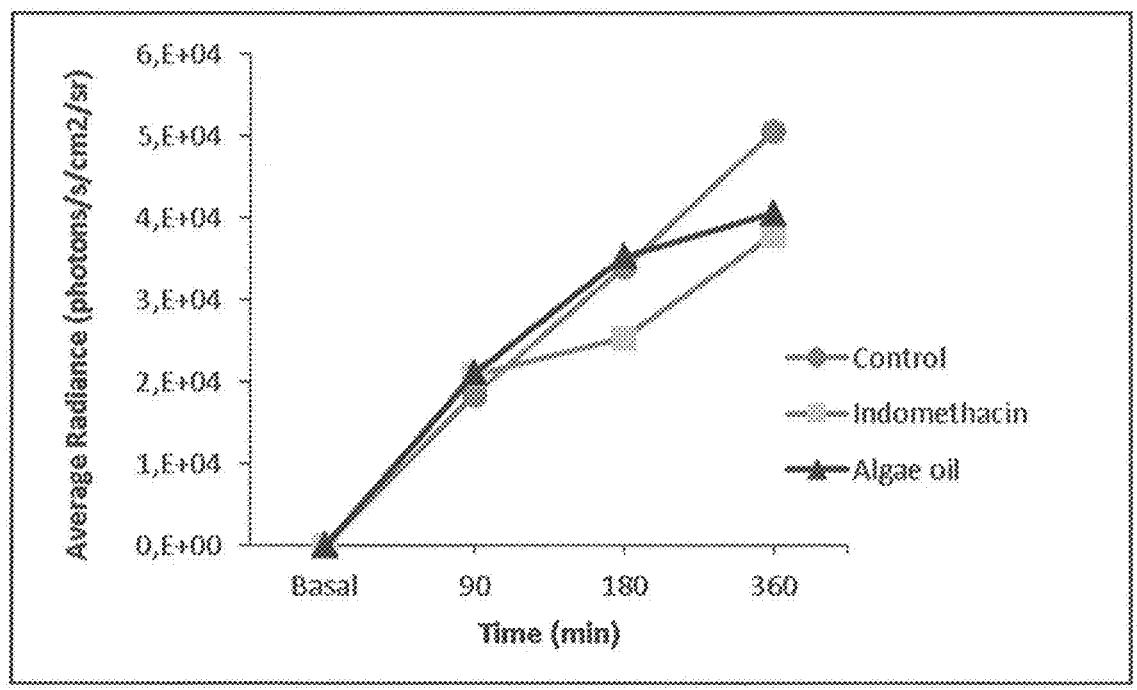

As shown in FIG. 6A, the total flux at time 180 min the value (photons/sec) for the Algae oil is 37% higher than the positive control indomethacin with a significant value of p<0.02.

However this difference between algae oil and the indomethacin decrease being at 360 min close to the indomethacin.

Example 5. Encapsulation of a Composition Containing EPA, DHA, 17-HDHA and 18-HEPE in a Capsule The oil fraction LM03-2 obtained in example 1 was encapsulated in an oval enteric soft gelatin shell.

The specifications of encapsulated LM03-2 composition in a capsule are shown in Table 9.

TABLE 9

Specifications of LM03-2 encapsulated

| | |
|---|---|
| Capsule weight | 423 mg |
| Contain weight | 256 mg |
| Weight variation | 97-102% |
| Specific gravity | 0.75 g/mL |
| Gastric disintegration | Conform |

TABLE 9-continued

| Specifications of LM03-2 encapsulated | |
|---|---|
| Intestinal disintegration | <15 min |
| Total acidity | 1.51 mg KOH/g |
| Cholesterol | 0.33 mg/capsule |
| Total Fat | 256 mg/capsule |
| Total Omega-3 | 169 mg/capsule |
| EPA | 75 mg/capsule |
| DHA | 25 mg/capsule |
| 17-HDHA | 12.5 mg/capsule |
| 18-HEPE | 10 mg/capsule |

Example 6. Emulsification of a Composition Containing EPA, DHA, 17-HDHA and 18-HEPE as Delivery Form The LM03-6 oil fraction obtained in Example 1 was mixed with demineralised water, emulsifiers, preservatives, stabilizers, natural flavours, pH controllers and sweeteners to provide an oral lipidic emulsion formed by a ordered network. This reaction is made at room temperature in absence of oxygen, by a previous blanketing step. At the end of the process, a pasteurization step is performed as micro-biological control.

The specification of the emulsified LM03-6 composition is shown in Table 10. The typical composition of the emulsified LM03-6 packed in a sachet is shown in Table 11.

TABLE 10

| Specifications of emulsified LM03-6. | | |
|---|---|---|
| Total Omega-3 (as FFA) | Min. 50 mg/g | Min. 5 wt. % |
| EPA (as FFA) | Min. 10 mg/g | Min. 1 wt. % |
| DHA (as FFA) | Min. 30 mg/g | Min. 3 wt. % |
| 17-HDHA | Min. 5 mg/kg | Min. 0.0005 wt. % |
| 18-HEPE | Min. 3 mg/kg | Min. 0.0003 wt. % |
| 17-HDHA + 18-HEPE | Min. 8 mg/kg | Min. 0.0008 wt. % |

TABLE 11

| Specifications of emulsified LM03-6 packed in a sachet. | | |
|---|---|---|
| Sachet 15 ml weight | 14.97 g | |
| Total Omega-3 (as FFA) | Min. 900 mg/sachet | Min. 6.012 wt. % |
| EPA (as FFA) | Min. 150 mg/sachet | Min. 1.002 wt. % |
| DHA (as FFA) | Min. 450 mg/sachet | Min. 3.006 wt. % |
| 17-HDHA | Min. 75 µg/sachet | Min. 0.0005 wt. % |
| 18-HEPE | Min. 60 µg/sachet | Min. 0.0004 wt. % |
| 17-HDHA + 18-HEPE | Min. 135 µg/sachet | Min. 0.0009 wt. % |

The invention claimed is:

1. A composition comprising:
omega-3 fatty acids present in an amount of about 20% to about 95%, by weight, of the composition; and
17-hydroxy-4Z,7Z,10Z,13Z,15E,19Z-docosahexaenoic acid ("17-HDHA"), 14-hydroxy-4Z,7Z,10Z,12E,16Z,19Z-docosahexaenoic acid ("14-HDHA") and 18-hydroxy-5Z,8Z,11Z,14Z,16E-eicosapentaenoic acid ("18-HEPE"), wherein the 17-HDHA is present in an amount of about 0.01% to about 0.04%, 18-HEPE is present in an amount of 0.02% to about 0.07%, and 14-HDHA is present in an amount of about 0.008% to about 0.04%, by weight, of the composition.

2. The composition of claim 1, wherein the composition is present in a capsule.

3. The composition of claim 1, wherein the omega-3 fatty acids comprise docosahexaenoic acid ("DHA") and/or eicosapentaenoic acid ("EPA").

4. The composition of claim 1, wherein the omega-3 fatty acids, 17-HDHA, and/or 18-HEPE are present in the composition as a free fatty acid, ester, phospholipid, mono-glyceride, di-glyceride, tri-glyceride, or combinations thereof.

5. The composition of claim 1, wherein the 17-HDHA is present in an amount of about 0.02%, by weight, of the composition.

6. The composition of claim 1, wherein the 18-HEPE is present in an amount of about 0.03%, by weight, of the composition.

7. The composition of claim 1, wherein the 18-HEPE is present in an amount of about 0.04%, by weight, of the composition.

8. The composition of claim 1, wherein 14-HDHA is present in an amount of about 0.01%, by weight, of the composition.

9. A dietary supplement, nutraceutical product, nutritional composition for infant formulae and/or prenatal formulae, pharmaceutical composition, vaccine coadjuvant, chemo-therapeutic coadjuvant or medical food composition comprising the composition of claim 1.

10. A method of treating inflammation comprising administering the composition of claim 1 to a subject having inflammation.

11. A composition comprising:
omega-3 fatty acids present in an amount of about 20% to about 95%, by weight, of the composition; and
17-HDHA, 18-HEPE, and 14-HDHA, wherein the 18-HEPE is present in an amount of about 0.03% to about 0.06%, the 17-HDHA is present in an amount of about 0.2%, and the 14-HDHA is present in an amount of about 0.01% to about 0.1%, by weight, of the composition.

12. The composition of claim 11, wherein the 14-HDHA is present in an amount of about 0.01%, by weight, of the composition.

13. The composition of claim 11, wherein the 14-HDHA is present in an amount of about 0.03%, by weight, of the composition.

14. The composition of claim 11, wherein the 18-HEPE is present in an amount of about 0.03%, by weight, of the composition.

15. The composition of claim 11, wherein the 18-HEPE is present in an amount of about 0.06%, by weight, of the composition.

16. The composition of claim 11, wherein the omega-3 fatty acids comprise DHA and/or EPA.

17. The composition of claim 11, wherein the omega-3 fatty acids, 17-HDHA, and/or 18-HEPE are present in the composition as a free fatty acid, ester, phospholipid, mono-glyceride, di-glyceride, tri-glyceride, or combinations thereof.

18. A method of treating inflammation comprising administering the composition of claim 11 to a subject having inflammation.

* * * * *